United States Patent [19]
Wang et al.

[11] Patent Number: 5,872,005
[45] Date of Patent: Feb. 16, 1999

[54] PACKAGING CELL LINES FOR ADENO-ASSOCIATED VIRAL VECTORS

[75] Inventors: Qing Wang, San Mateo; Mitchell H. Finer, San Carlos; Xiao-Chi Jia, Belmont, all of Calif.

[73] Assignee: Cell Genesys Inc., Foster City, Calif.

[21] Appl. No.: 439,586

[22] Filed: May 12, 1995

Related U.S. Application Data

[63] Continuation of Ser. No. 333,680, Nov. 3, 1994.

[51] Int. Cl.$^6$ .............................. C12N 15/00; C12N 5/08
[52] U.S. Cl. ........................................ 435/320.1; 435/369
[58] Field of Search .............................. 435/320.1, 177.3, 435/240.2, 235.1, 91.4, 240.1, 69.1, 375, 369; 514/44

[56] References Cited

U.S. PATENT DOCUMENTS

| | | | |
|---|---|---|---|
| 5,354,678 | 10/1994 | Lebkowski et al. | 435/172.3 |
| 5,436,146 | 7/1995 | Shenk et al. | 435/172.3 |
| 5,474,935 | 12/1995 | Chatterjee et al. | 435/320.1 |

OTHER PUBLICATIONS

Hermonat et al. 1984 Journal of Virology 51(2) 329–339.
Su et al. 1992 Biochem/Biophys. Res. Comm. 186(1) 293–300.
Gossen et al. 1992 Proc. Nat'l Acad. Sci 89: 5547–5551.
Janik et al. 1989 Virology 168:320–329.

*Primary Examiner*—James Ketter
*Assistant Examiner*—Irem Yucel
*Attorney, Agent, or Firm*—Pennie & Edmonds LLP

[57] ABSTRACT

The present invention is directed to novel replication-deficient adenoviral vectors characterized in that they harbor at least two lethal early region gene deletions (E1 and E4) that normally transcribe adenoviral early proteins. These novel recombinant vectors find particular use in human gene therapy treatment whereby the vectors additionally carry a transgene or therapeutic gene that replaces the E1 or E4 regions. The present invention is further directed to novel packaging cell lines that are transformed at a minimum with the adenoviral E1 and E4 gene regions and function to propagate the above novel replication-deficient adenoviral vectors.

15 Claims, 14 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GCGCAAGCTT CGGGAGTGGG AGATAAGGCT C     3 1

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GGCCTCTAGA AGTTCACTTG CCCTGATGAC A     3 1

PACKAGING CELL LINES FOR ADENO-ASSOCIATED VIRAL VECTORS

This application is a continuation application of application Ser. No. 08/333,680, filed Nov. 3, 1994, which is pending.

FIELD OF THE INVENTION

The present invention relates to novel replication-deficient adenoviral vectors, novel packaging cell lines and recombinant adenoviruses for human gene therapy. In particular, the novel packaging cell lines have the complementary function for the early gene region E1, E4 and optionally the E3 deletions of human adenovirus.

BACKGROUND OF THE INVENTION

Replication-defective retroviral vectors as gene transfer vehicles provide the foundation for human gene therapy. Retroviral vectors are engineered by removing or altering all viral genes so that no viral proteins are made in cells infected with the vector and no further virus spread occurs. The development of packaging cell lines which are required for the propagation of retroviral vectors were the most important step toward the reality of human gene therapy. The foremost advantages of retroviral vectors for gene therapy are the high efficiency of gene transfer and the precise integration of the transferred genes into cellular genomic DNA. However, major disadvantages are also associated with retroviral vectors, namely, the inability of retroviral vectors to transduce non-dividing cells and the potential insertional mutagenesis.

Human adenoviruses have been developed as live viral vaccines and provide another alternative for in vivo gene delivery vehicles for human gene therapy [Graham & Prevec in New Approaches to Immunological Problems, Ellis (ed), Butterworth-Heinemann, Boston, Mass., pp. 363–390 (1992) Rosenfeld, et al, Science 252: 431–434 (1991), Rosenfeld, et al, Cell 68: 143–155 (1992), and Ragot, et al, Nature 361: 647–650 (1993)]. The features which make recombinant adenoviruses potentially powerful gene delivery vectors have been extensively reviewed [Berkner, Biotechniques 6: 616–629, (1988) and Kozarsky & Wilson, Curr. Opin. Genet. Dev. 3: 499–503, (1993)]. Briefly, recombinant adenoviruses can be grown and purified in large quantities and efficiently infect a wide spectrum of dividing and non-dividing mammalian cells in vivo.

Moreover, the adenoviral genome may be manipulated with relative ease and accommodate very large insertions of DNA.

The first generation of recombinant adenoviral vectors currently available have a deletion in the viral early gene region 1 (herein called E1 which comprises the E1a and E1b regions from genetic map units 1.30 to 9.24) which for most uses is replaced by a transgene. A transgene is a heterologous or foreign (exogenous) gene that is carried by a viral vector and transduced into a host cell. Deletion of the viral E1 region renders the recombinant adenovirus defective for replication and incapable of producing infectious viral particles in the subsequently infected target cells [Berkner, Biotechniques 6: 616–629 (1988)]. The ability to generate E1-deleted adenoviruses is based on the availability of the human embryonic kidney packaging cell line called 293. This cell line contains the E1 region of the adenovirus which provides the E1 region gene products lacking in the E1-deleted virus [Graham, et al, J. Gen Virol. 36: 59–72, (1977)]. However, the inherent flaws of current first generation recombinant adenoviruses have drawn increasing concerns about its eventual usage in patients. Several recent studies have shown that E1 deleted adenoviruses are not completely replication incompetent [Rich, Hum. Gene. Ther. 4: 461–476 (1993) and Engelhardt, et al, Nature Genet. 4: 27–34 (1993)]. Three general limitations are associated with the adenoviral vector technology. First, infection both in vivo and in vitro with the adenoviral vector at high multiplicity of infection (abbreviated m.o.i.) has resulted in cytotoxicity to the target cells, due to the accumulation of penton protein, which is itself toxic to mammalian cells [(Kay, Cell Biochem. 17E: 207 (1993)3. Second, host immune responses against adenoviral late gene products, including penton protein, cause the inflammatory response and destruction of the infected tissue which received the vectors [Yang, et al, Proc. Natl, Acad. Sci. USA 91: 4407–4411 (1994)]. Lastly, host immune responses and cytotoxic effects together prevent the long term expression of transgenes and cause decreased levels of gene expression following subsequent administration of adenoviral vectors [Mittal, et al, Virus Res.28: 67–90 (1993)].

In view of these obstacles, further alterations in the adenoviral vector design are required to cripple the ability of the virus to express late viral gene proteins, decreasing host cytotoxic responses and the expectation of decreasing host immune response. Engelhardt et al recently constructed a temperature sensitive (ts) mutation within the E2A-encoded DNA-binding protein (DBP) region of the E1-deleted recombinant adenoviral vector [Engelhardt, et al, Proc. Natl. Acad. Sci. USA 91: 6196–6200 (1994)] which fails to express late gene products at non-permissive temperatures in vitro. Diminished inflammatory responses and prolonged transgene expression were reported in animal livers infected by this vector (Engelhart, et al 1994). However, the ts DBP mutation may not give rise to a full inactive gene product in vivo, and therefore be incapable of completely blocking late gene expression. Further technical advances are needed that would introduce a second lethal deletion into the adenoviral E1-deleted vectors to completely block late gene expression in vivo. Novel packaging cell lines that can accommodate the production of second (and third) generation recombinant adenoviruses rendered replication-defective by the deletion of the E1 and E4 gene regions hold the greatest promise towards the development of safe and efficient vectors for human gene therapy. The present invention provides for such packaging cell lines and resultant mutant viruses and recombinant viral vectors (for example, adenoviral or AAV-derived) carrying the transgene of interest.

SUMMARY OF THE INVENTION

Accordingly, the present invention generally aims to provide an improved adenoviral vector system to obviate the difficulties found in using the first generation adenoviral vectors currently available by providing second and third generation viral vectors deleted of at least two early region DNA sequences, and that are capable of delivering foreign, therapeutic or transgenes to somatic cells.

In particular, the present invention provides for second and third generation recombinant adenoviral vectors (adenoviruses) harboring at least two lethal deletions, namely, the E1 and E4 early region genes. Optionally, this vector may also be deleted of the E3 early gene region. More particularly, this recombinant viral vector carries a transgene, for example, the β-galactosidase gene, introduced into either the E1 or E4 regions. In a more particular embodiment, the recombinant adenoviruses may contain a therapeutic gene that replaces the E1 or E4 regions (or optionally the E3 region), and the therapeutic gene is expressed and/or transcribed in a targeted host cell.

Another object of the present invention is to provide a novel packaging cell line which complements functions of the E1, E4 and optionally the E3 gene regions of a defective adenovirus deleted of the E1, E4 and optionally E3 regions, thereby allowing the production of the above described second generation recombinant adenoviral vectors deficient of the E1, E4 and optionally, the E3 DNA regions. The preferred packaging cell line derived from human embryonic kidney cells (293 cell line) contains the adenovirus E1 and E4 gene regions integrated into its genome. In a particular embodiment, the packaging cell line is identified herein as 293-E4 and deposited on Aug. 30, 1994, with the American Type Culture Collection (ATCC), 12301 Parklawn Drive, Rockville, Md., under the Budapest Treaty, and has there been designated ATCC #CRL 11711.

Another object of the present invention is to provide a plasmid used to introduce the E4 region into the 293 cells. The bacterial plasmid comprises the adenovirus E4 region devoid of the E4 promoter and substituted with an inhibin promoter. In a particular embodiment, the plasmid comprises the adenovirus described above and a mouse alpha ($\alpha$)-inhibin promoter which is identified as pIK6.1 MIP($\alpha$)-E4 and deposited at the ATCC on Aug. 30, 1994, under the Budapest Treaty, and has there been designated ATCC #75879.

Yet another object of the present invention is to provide a method of infecting a mammalian target cell with the above-identified second or third generation recombinant viral vectors that carry transgenes for in vivo and ex vivo gene therapy.

Panel B represents 293 cells with a mock infection and an addition of 1 mM of cAMP.

Figure 5:
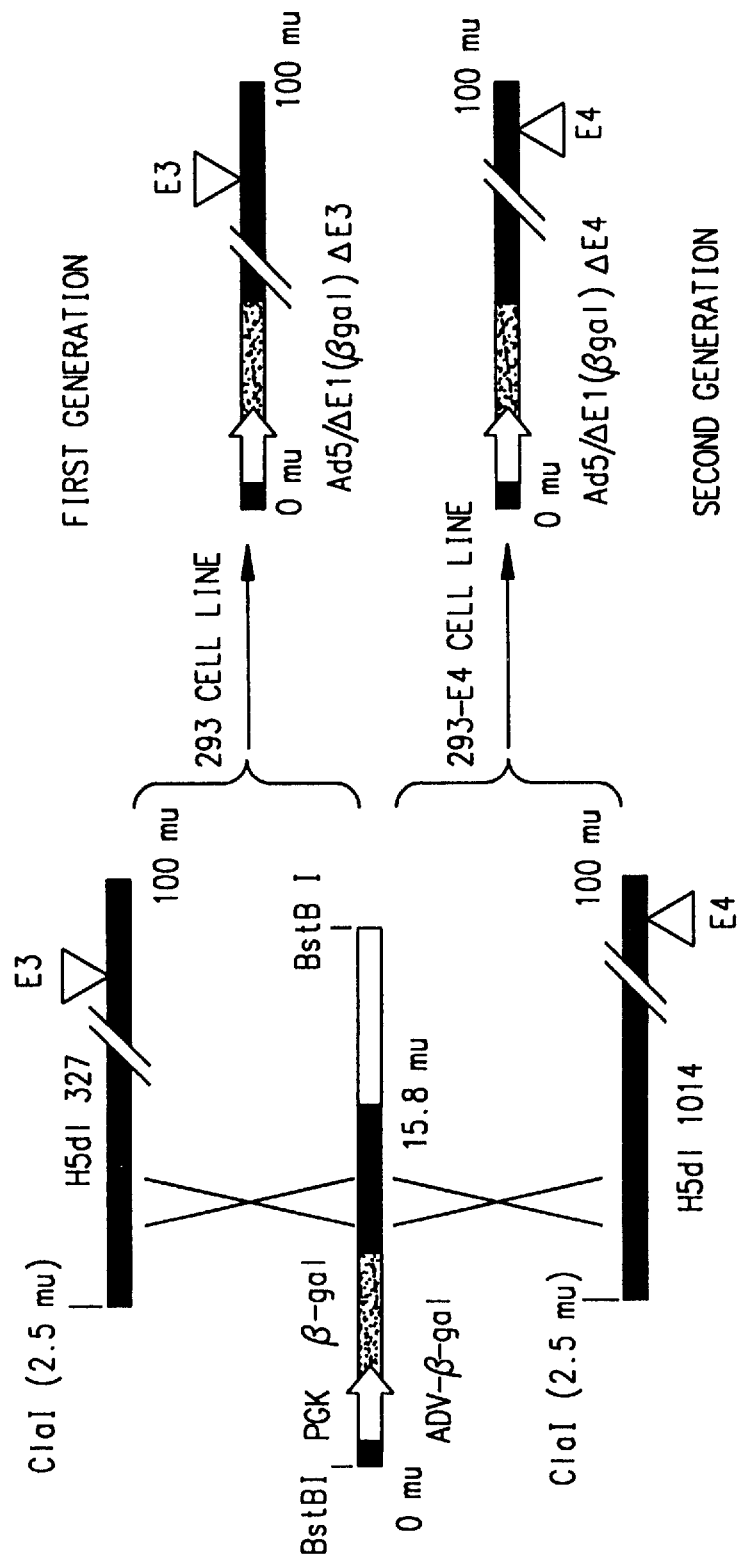

FIG. 5 depicts the construction and the structure of recombinant viruses Ad5/$\Delta$E1($\beta$-gal)$\Delta$E4 and Ad5/$\Delta$Ea($\beta$-gal)$\Delta$E3, as described in Example 5, infra.

Figure 6:
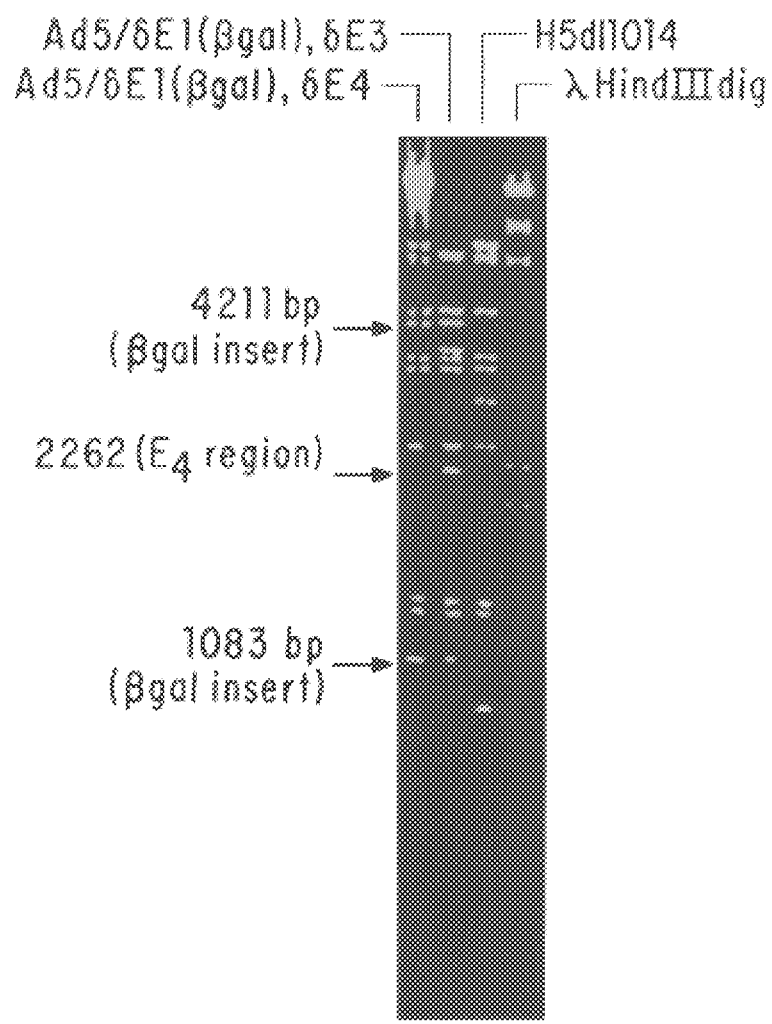

FIG. 6 illustrates the restriction enzyme analysis of recombinant viruses, as described in Example 5, infra.

DETAILED DESCRIPTION OF THE INVENTION

One strategy designed to circumvent the problems associated with current early region-deleted adenoviral vectors is to introduce a second essential gene region deletion into the adenoviral vector. Several adenovirus early gene region transformed cell lines which support the growth of E1, E2A or E4 mutant virus growth, respectively, have been established [Grahan, et al, *J. Gen Virol.* 36: 59–72 (1977), Weinberg, et al, *Proc. Natl. Acad. Sci. USA* 80: 5383–5386 (1983) and Brough, et al, *Virology* 190: 624–634 (1992)]. However, no cell line offers the functions of two gene regions simultaneously and at permissive temperatures. Establishing such a cell line which possesses the capability to complement the E1 and a second essential gene region function in trans (eg., E4), and the capacity to function as a packaging cell line for the propagation of recombinant viral vectors containing such double (or possibly triple or quadruple) deletions, may eliminate the drawbacks of the first generation adenoviral vectors currently available.

Studies of the adenovirus early region (ER) gene functions have shown that the deletion of the E4 region results in a failure to accumulate viral late transcripts; a reduction in viral late protein synthesis; a defective viral particle assembly and a failure to inhibit host protein synthesis at the late infection stage [Sandler, et al, *J. Virol.* 63: 624–630 (1989), Bridge & Ketner, *Virology* 174: 345–353 (1990), Ross & Ziff, *J. Virol.* 66: 3110–3117 (1992), Bridge, et al, *Virology* 193: 794–801 (1993), and Bett, et al, *J. Virol.* 67: 5911–5921 (1993)]. Dual removal of the E1 and E4 gene regions from the recombinant adenovirus vectors may therefore dramatically minimize or eliminate the pathogenic effects of direct cytotoxicity to the targeted cells and inflammatory responses in the human body. The E4 deletion in a second generation recombinant adenoviral vector would provide the additional benefit of increasing the capacity of this vector system to accommodate human gene inserts as large as 10 kb.

In one aspect of the present invention, the successful establishment of a novel packaging cell line which supports the growth of both the E1 and E4 deletions in E1 and E4 deficient adenoviruses has been demonstrated. Since one of the E4 gene products [294R protein of open reading frame (ORF) 6] in association with the E1b gene product (496R protein) has a function of inhibiting cellular mRNA transport resulting in the cessation of cellular protein synthesis (Bridge & Ketner, 1990), the overexpression of the E4 gene region would be expected to ultimately result in cell death. A major obstacle to the introduction of the E4 gene region into 293 cells has been overcome, i.e., the trans activation of the E1a gene product in the parental 293 cells which causes the overexpression of the E4 genes which would otherwise result in cell death. In the present invention, the E4 promoter is replaced with a cellular inducible hormone gene promoter, namely, a gene that is regulated by a nuclear factor called CRE binding protein (CREB). Particularly, the promoter that replaces the E4 promoter is chosen from the CREB regulated gene family such as $\alpha$-inhibin, beta ($\beta$)-inhibin, α-gonadotropin, cytochrome c, cytochrome c oxidase complex (subunit IV), glucagon, etc. listed in Table I on page 15695 in Kim, et al, *J. Biol Chem.,* 268: 15689–15695 (1993). In a preferred embodiment, the CREB regulated gene promoter is a mammalian α-inhibin, most preferably, mouse α-inhibin. In this instance, a 165 base pair sequence of the mouse inhibin promoter region has been shown to drive the heterologous gene expression at a low basal level and increase the levels of heterologous gene expression in response to the induction of cAMP or adenylic cyclase activators [Su & Hsueg, *Biochem. and Biophys. Res. Common.* 186, 293–300 (1992)]. An 8 bp palindromic sequence called cAMP response element (CRE) is responsible for this inductory effect and has been identified within the inhibin promoter region. In fact, all adenovirus early gene promoters contain the CRE-like element which renders these early genes responsive to the induction of cAMP (Jones, et al, *Genes Dev.* 2: 267–281 (1988)]. It is clear that E1a trans activation and the cAMP enhancement act on adenovirus early genes via independent mechanisms [Leza & Hearing, *J. Virol.* 63: 3057–3064 (1989) and Lee, et al, *Mol. Cell. Biol.* 9: 4390–4397 (1989)]. The replacement of the E4 promoter with the mouse α-inhibin promoter uncouples the E1a trans-activation from the cAMP induction on the E4 gene. In the present invention, a full length sequence of the E4 region is introduced into the 293 cells whereby the cAMP induction is still effective in inducing E4 gene expression in the transformed cells in a controlled manner. It should also be noted that this novel 293-E4 packaging cell line may also rescue (supports the growth of) adenoviruses containing the E3 deletion in addition to the E1 and E4 deletions because the deletion of the E3 region will not affect the viability of the virus.

The novel 293-E4 packaging cell lines were stably transformed by the E4 region and displayed the same morphology and the growth rate as parental 293 cells. This indicates that the low level of E4 gene expression under the control of the mouse α-inhibin promoter does not cause extensive inhibition of host cell protein synthesis. The mutant adenovirus, H5dl1014 [Bridge, et al, *Virology* 193: 794–801 (1993)], was used to examine the complementing activity of the above described 293-E4 packaging cell line because it carries lethal deletions in the E4 region and can only grow in W162 cells (Bridge, & Ketner, 1989). The W162 cell line is a Vero monkey kidney cell line transformed by adenovirus E4 DNA and complements the growth of E4 deletion adenoviruses. The H5dl1014 virus has been shown to produce markedly reduced levels of DNA and failed to synthesize late protein due to an intact ORP 4 [Bridge, et al, (1993)] in its mostly deleted E4 region. Cell lines were found that produced the H5dl1014 virus at comparable titers to that produced in W162 cells (See Table IV, Groups 1 and 2 in Example 11, infra).

In another embodiment, the present invention relates to novel recombinant adenoviruses or mutant adenoviruses produced by the novel packaging cell lines of the present invention. As described herein, the term "recombinant adenovirus" or "recombinant adeno-associated virus" (also known as recombinant viral vectors in the art) refers to a virus wherein the genome contains deletions, insertions and/or substitutions of one or more nucleotides, and the virus further carries a transgene. The term "mutant virus" refers herein to a particular virus, for example adenovirus and AAV, wherein the genome contains deletions, insertions and/or substitutions of one or more nucleotides; however no transgene is carried in the mutant virus. In one particular aspect of this embodiment, the novel 293-E4 packaging cell lines described above are used to generate a second generation of recombinant virus called Ad5/ΔE1(β-gal)ΔE4. Although the 293-E4 packaging cell line contains the adenoviral serotype 5 E1 and E4 gene regions, other serotypes of mutant and recombinant adenoviruses, for example, serotype 2, 7 and 12, may be rescued due to the high degree of structural and functional homology among the adenoviral serotypes. Moreover, mutant and recombinant adenoviruses from serotypes other than serotype 5 may be rescued from the other novel adenoviral packaging cell lines of the present invention described infra.

In vitro studies demonstrate that the infection of the novel recombinant adenovirus vectors of the present invention in non-permissive human cells show no cytopathic effects and the efficiency of the transgene expression is at levels comparable to conventional E1-deleted viruses. It is expected that the host immune responses and inflammatory reactions at the sites infected with novel second generation recombinant adenoviruses of the present invention will be reduced compared to the first generation recombinant adenoviruses currently available. The establishment of the dual complementing packaging cell line of the present invention marks a significant event in the evolution of safer and more effective gene transfer adenoviral vectors. The method used in the construction of the 293-E4 cell lines of the present invention is of general utility in the production of other packaging cell lines which contain additional adenoviral regions which complement further deletions of the adenoviral vectors of the present invention or in the construction of other viral vectors.

Thus, in another embodiment, the present invention relates to novel adenoviral packaging cell lines that can rescue deletions in addition to E1, E4 and optionally E3 by the methods described above. In this example, an adenoviral vector packaging cell line which can rescue the E2A mutation, in addition to the E1, E3 and E4 deletions, was constructed starting with the novel packaging cell line described above, namely the 293-E4 packaging cell line. The E2A gene product is a regulatory protein, specifically, a DNA binding protein. This gene may be introduced into the 293-E4 packaging cell line by placing the E2A gene under the control of an inducible promoter operably linked to the E2A gene in a similar manner as described above. The inducible promoter may be selected from the same family of CREB regulated genes described above used to replace the E2 gene promoter.

In yet another embodiment, the present invention relates to an adenoviral vector packaging cell line that may rescue the adenovirus recombinant virus containing the minimum essential cis-elements (inverted terminal repeats (ITRs) and packaging signal sequence) [Hering, et al, *Virol.* 61: 2555–2558 (1987)] and protein IX sequence [Ghosh-Choudury, et al, *EMBO J.* 6: 1733–1739 (1987)] only. This cell line may be established by introducing the adenovirus DNA sequence from around m.u. 11.2 to approximately 99 into the novel 293-E4 cell line described above. This DNA sequence represents the sequence from after E1b gene to the 3' end of the viral structural gene [Sanbrook, et al, *Cold Spring Harbor Symp. Quant. Biol.* 39: 615–632 (1974); Ziff & Evans, *Cell* 15: 1463–1476 (1978)]. The introduced adenovirus sequence contains viral structural genes and almost the entire functional gene regions except E1a and E1b. Because the constitutive expression or overexpression of viral gene products are very toxic to the cells, the introduced adenoviral DNA may be manipulated to replace adenoviral native promoters with heterologous promoters. For example, the early gene regions which encode viral regulatory proteins may be placed under the control of the CREB regulated promoters, which have about 2 to 10 fold induction efficiency. In the case of the gene region that encodes viral structural proteins, the native major late promoter may be replaced by a tightly controlled exogenous promoter such as the tetracycline-responsive promoter which has an induction level up to about $10^5$ fold in the presence of tetracycline [Manfred & Hermann, *PNAS* 89: 5547–5551 (1992)].

In another embodiment, the present invention relates to novel adenoviral-associated (AAV) packaging cell lines prepared in the following manner. The novel complementing cell line contains the E1a, E1b, E2A, and E4 gene regions and the DNA sequence encoding virus-associated RNA. This cell line may be constructed by introducing the adenovirus DNA sequence encoding the virus-associated RNA (around 200 NTs from m.u. 29 [Mathews, *Cell* 6: 223–229 (1975) and Petterson & Philipson, *Cell* 6: 1–4 (1975)] into the novel 293-E4 packaging cell line constructed above that rescues the E1 and E4 deletions, the E2A mutation of adenovirus and optionally E3. The wild type AAV produced from this packaging cell line will be free of helper adenovirus. The recombinant adeno-associated virus or mutant AAV will only contain the minimal essential cis-elements and will be generated by co-transfecting a non-packaging complementing AAV plasmid which is defective for packaging but supplies the wild type AAV gene products [Samulski et al, *J. Virol.* 61: 3096–3101 (1987)]. Moreover, the recombinant adeno-associated viral vectors or mutant AAV rescued from this cell line will be free of helper viruses, i.e., adenoviruses.

In another embodiment, the present invention relates to yet another novel AAV packaging cell line constructed by starting with the AAV packaging cell line described above. This packaging cell line contains the E1a, E1b, E2A and E4 gene regions, the DNA encoding virus-associated RNA and additionally, the AAV virus replication (rep) gene regions. The rep gene region encodes at least four replication (Rep) proteins that are essential for AAV DNA replication and trans-regulation of AAV gene expression [(for review, see Bervis & Bolienzsky, *Adv. Virus Res.* 32: 243–306 (1987)]. It is constructed by introducing the AAV rep gene region into the AAV packaging line described above that already contains the E1, E2A, E4 gene regions and DNA sequences encoding the virus-associated RNA in the manner that replaces the P5 promoter [(Yang, et al, *J. Virol.* 68: 4847–4856 (1994)] with an inducible promoter chosen from the CREB regulated gene family described previously. The novel AAV virus and its recombinant virus rescued from the cell line will be free of helper viruses (adenoviruses) and is Rep-[Muzyczka, *Curr. Top. Microbiol. Immunol.* 158: 97–129 (1992)].

In another embodiment, the present invention relates to another novel AAV packaging cell line constructed by starting with the AAV packaging cell line described in the previous paragraph. This packaging cell line contains the E1a, E1b, E2A, E4 gene regions, the DNA encoding the virus-associated RNA, the AAV virus replication (rep) gene region, and additionally the AAV cap gene region. The cap gene region encodes a family of capsid proteins, i.e., VP1, VP2 and VP3 [Janik, et al, *J. Virol.* 52: 591–597 (1984)]. The synthesis of all three mRNAs are started from a single promoter called P40 [Janik, et al, (1984)]. This gene region will be introduced into the AAV packaging cell line described above by replacing the P40 promoter with an inducible promoter selected from either the CREB regulated promoters or the tetracycline responsive promoter. The novel AAV virus and its recombinant virus rescued from the cell line will be free of helper viruses (adenoviruses) and only contain the minimal essential cis-elements [Muzyczka, *Curr. Top. Microbiol. Immunol.* 158: 97–129 (1992)].

The present invention further provides the production of novel mutant viruses (particularly, adenoviruses and AAV), and novel recombinant adenoviruses and AAV (also referred to herein as recombinant adenoviral-derived and AAV-derived vectors) containing a transgene which will be expressed in the target cells. The recombinant adenoviral-derived and AAV-viral vectors are prepared using the packaging cell lines described above which comprise one or more distinct nucleotide sequences capable of complementing the part of the adenovirus or AAV genome that is essential for the virus' replication and which is not present in the novel recombinant adenoviral-derived and AAV-derived vectors. Recombinant adenoviral-derived and AAV-derived vectors will no longer contain genes required for the virus replication in infected target cells. More particularly, the recombinant adenoviral vectors will only contain the minimum essential cis-elements (i.e., ITRs and packaging signal sequence) and protein IX sequence, and be free of the E1 (specifically, E1a and E1b) and E4 regions, and may additionally be free of E3 and E2A regions and the viral structural genes. In the case of the recombinant AAV vectors, these vectors will contain deletions of the AAV virus Rep protein coding region or will only contain the minimal essential cis-elements. The latter will be generated from the AAV packaging cell line which contains the E1a, E1b, E2A and E4 gene regions, and the DNA encoding virus-associated RNA by co-transfecting a non-packaging complementing AAV plasmid which is defective for packaging but supplies the wild type AAV gene products [Samulski, et al, (1987)].

The recombinant adenovirus-derived or AAV-derived vector is also characterized in that it is capable of directing the expression and the production of the selected transgene product(s) in the targeted cells. Thus, the recombinant vectors comprise at least all of the sequences of the adenoviral or AAV DNA sequence essential for encapsidation and the physical structures for infection of the targeted cells and a selected transgene which will be expressed in the targeted cells.

The transgene may be a therapeutic gene that will ameliorate hereditary or acquired diseases when expressed in a targeted cell by using gene transfer technology methods well known in the art. In one particular aspect, the therapeutic gene is the normal DNA sequence corresponding to the defective gene provided in Table I below, for example, the normal DNA sequence corresponding to LDL receptors and α 1-antitrypsin. In another aspect, the transgene may encode a cytokine gene, suicide gene, tumor suppressor gene or protective gene, or a combination thereof chosen from the list provided in Table II. If a cytokine gene is selected, the expression of the gene in a targeted cell may provide a treatment to malignancies by stimulating cellular immune responses which result in suppression of tumor growth and/or killing of tumor cells. If a suicide gene is chosen, the gene when expressed in the tumor cell will enable the tumor cell to be destroyed in the presence of specific drugs. For example, the thymidine kinase gene when expressed in tumor cells will enable the tumor to be destroyed in the presence of gancyclovir.

In yet another embodiment, the transgene may encode a viral immunogenic protein that is utilized as a vaccine for prevention of infectious diseases (See Table III). Procedures for preparing and administering such vaccines are known in the art (see e.g., Estin, et al, *Proc. Nat. Acad. Sci.* 85:1052 (1988)).

The present invention further relates to therapeutic methods for the treatment of hereditary and acquired diseases, cancer gene therapies, and vaccines for prevention of infectious diseases. The transgene may be expressed under the control of a tissue specific promoter. For example, a suicide gene under the control of the tyrosinase promoter or tyrosinase related protein-1 promoter will only be expressed in melanocytes in the case of cancer therapy for melanoma [Vile & Hart, *Cancer Res.* 53: 962–967 (1993) and Lowings, et al, *Mol. Cell. Biol.* 12: 3653–3663 (1992)]. Various methods that introduce an adenoviral or AAV vector carrying a transgene into target cells ex vivo and in vivo have been previously described and are well known in the art. [See for example, Brody & Crystal, Annals of N.Y. Acad. Sci. 716: 90–103, 1993]. The present invention provides for therapeutic methods, vaccines, and cancer therapies by infecting targeted cells with the recombinant adenoviral or AAV vectors containing a transgene of interest, and expressing the selected transgene in the targeted cell.

For example, in vivo delivery of recombinant adenoviral or AAV vectors containing a transgene of the present invention may be targeted to a wide variety of organ types including brain, liver, blood vessels, muscle, heart, lung and skin. The delivery route for introducing the recombinant vectors of the present invention include intravenous, intramuscular, intravascular and intradermal injection to name a few routes. (See also Table I in the Brody & Crystal article and the references cited.)

In the case of ex vivo gene transfer, the target cells are removed from the host and genetically modified in the laboratory using AAV-vectors of the present invention and methods well known in the art [Walsh, et al, *PNAS* 89: 7257–7261, (1992) and Walsh et al, *Proc. Soc. Exp. Bio. Med.* 204: 289–300 (1993)].

Thus, the recombinant adenoviral or AAV vectors of the invention can be administered using conventional modes of administration including, but not limited to, the modes described above. The recombinant adenoviral or AAV vectors of the invention may be in a variety of dosages which include, but are not limited to, liquid solutions and suspensions, microvesicles, liposomes and injectable or infusible solutions. The preferred form depends upon the mode of administration and the therapeutic application.

TABLE I

Gene Therapy for Hereditary Disease

| DISEASES | DEFECTIVE GENES | GENE PRODUCTS |
|---|---|---|
| Familial hypercholesterolemia (type II hyperlipidemias) | LDL receptor | LDL receptor |
| Familial lipoprotein lipase deficiency (type I hyperlipidmias) | Lipoprotein lipase | Lipoprotein lipase |
| Phenylketonuria | Phenylalanine hydroxylase | Phenylalanine hydroxylase |
| Urea cycle deficiency | Ornithine transcarbamylase | Ornithine transcarbamylase |
| Von Gierke's disease (glycogen storage disease, type I) | G6Pase | Glucose-6-phosphotase |
| Alpha I-antitrypsin deficiency | Alpha 1-antitrypsin | Alpha 1-antitrypsin |
| Cystic fibrosis | Cystic fibrosis transmembrane conductant regulator | Membrane chlorine channel |
| Von Willebrand's disease and Hemophilia A | Factor VIII | Clotting factor VIII |
| Hemophilia B | Factor IX | Clotting factor Ix |
| Sickle cell anemia | Beta globin | Beta globin |
| Beta thalassemias | Beta globin | Beta globin |
| Alpha thalassemias | Alpha globin | Alpha globin |
| Hereditary sperocytosis | Spectrin | Spectrin |
| Severe combined immune deficiency | Adenosine deaminase | Adenosine deaminase |
| Duchenne muscular dystrophy | Dystrophin minigene | Dystrophin |
| Lesch-Nyhan syndrome | Hypoxanthine guanine phosphoribosyl transferase (HGPRT) | HGPRT |
| Gaucber's disease | Beta-glucocerebrosidase | Beta-glucocerebrosidase |
| Nieman-Pick disease | Sphingomyelinase | Sphingomyelinase |
| Tay-Sachs disease | Lysosomal hexosaminidase | Lysosomal hexosaminidase |
| Maple syrup urine disease | Branched-chain keto acid dehydrogenase | Branced-chain keto acid dehydrogenase |

TABLE II

Cancer Gene Therapy

| CYTOKINE GENES | SUICIDE GENES | TUMOR SUPPRESSOR GENES | PROTECTIVE GENES |
|---|---|---|---|
| IFN-gamma, IL-2, IL4, and granulocyte-macrophage colony stimulation factor | thymidine kinase, cytosine deaminase, diphtheria toxin, and TNF | p53, Rb, and Wt-1 | multiple drug resistant |

TABLE III

Vaccine for Infectious Disease

| DISEASES | VACCINE |
|---|---|
| Hepatitis | HBV surface antigen |
| HIV infection and AIDS | HIV envelope proteins |
| Rabies | Rabies glycoproteins |

The following examples are presented to illustrate the present invention and are not intended in any way to otherwise limit the scope of this invention.

EXAMPLES

Example 1

Construction of Plasmids

This example describes the construction of the plasmids used to introduce the E4 gene region into the 293 cells. The constructed plasmids are diagrammatically represented in FIG. 1. The parental plasmid pIK6.1 MMSV-E4 (ΔE4 pro.) derived from the pIK6.1 MMSV enpoNhe(Hpa) [Finer, et al, Blood 83: 43–50, (1994)] contains the promoterless E4 region from 15 bp upstream of the transcription start site to 810 bp downstream of the E4 polyadenylation site. The E4 gene is linked to the Moloney murine sarcoma virus U3 fragment. The pIK6.1. MIP(α)-E4 was constructed by ligation of a 238 bp fragment of the Hind III-XbaI PCR product of mouse alpha inhibin promoter [MIP(α)] (Su, & Hsueh, Biochem. and Biophys. Res. Common. 186: 293–300, 1992) with the 2.9 kb XbaI-StuI fragment and the 3.9 kb Stu I-Hind III fragment of the PIK6.1 MMSV-E4 (E4 pro.). The primers used for PCR of the MIP (α) were 5'-gcgcaagcttcGGGAGTGGGAGATAAGGCTC-3' (SEQ ID NO:1) and 5'-ggcctctagaAGTTCACTTGCCCTGATGACA-3' (SEQ ID NO:2). The sequences containing either the Hind III site or Xba I site in lower case are present to facilitate cloning. The cloned α-inhibin promoter was sequenced to verify the accuracy of the sequence.

Figure 2:
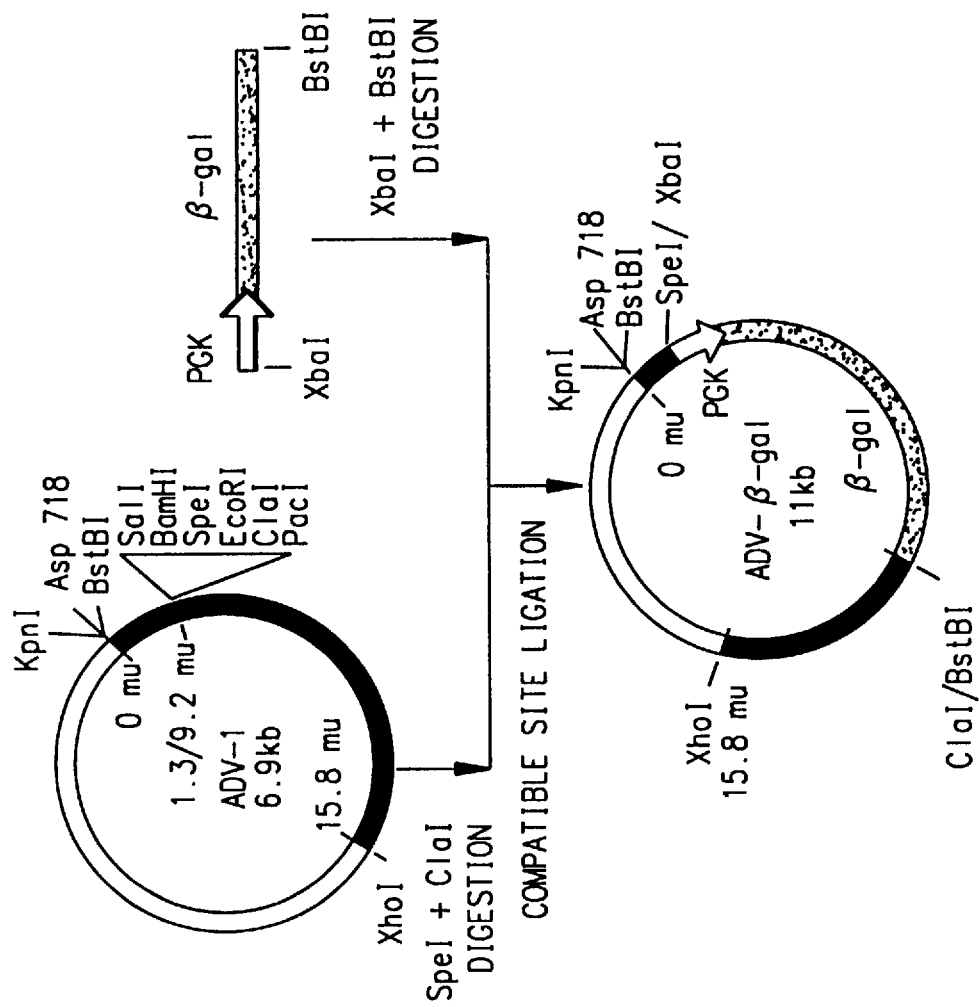
FIG. 2 depicts the construction of the ADV-$\beta$-gal plasmid, as described in Example 1, infra.

The plasmid ADV-β-gal used to generate recombinant adenoviruses was constructed as shown in FIG. 2. The starting plasmid ADV-1 contains the left end of adenovirus 5 Xho I C fragment (m.u. 0–15.8) with a deletion from nucleotides 469–3326 (m.u. 1.3–9.24) on the backbone of PCR II (In Vitrogen, San Diego, Calif.). A polylinker cassette was inserted into the deletion site. Several restriction sites at the left end of the adenovirus sequence can be conveniently used to linearize the plasmid. The resulting ADV-β-gal plasmid was constructed by insertion of a Bst BI-Xba I fragment of the E. coli β-galactosidase gene driven by the mouse pgk promoter into the ADV-1 compatible sites Spe I and Cla I in the E1 region and was later used to generate the recombinant virus.

Example 2

Transfection and Selection of 293-E4 Cell Lines

This example describes the transfection and selection process employed to establish 293-E4 cell lines. The 293 cells, obtained from the American Type Culture Collection, ATCC #CRL 1573, were grown in Dulbecco's modified Eagle's medium (DMEM), 1 g/L glucose (JRH Biosciences), 10% donor calf serum (Tissue Culture Biologics). Cells were seeded at 5×10⁵ per 10-cm plate 48 hours prior to the transfection experiment. Ten μg of pIK.MIP(α)-E4 and 1 μg of pGEM-pgkNeo.pgkpolyA containing the Neo$^r$ gene were co-transfected into 293 cells by calcium phosphate co-precipitation [Wigler, et al, Cell 57: 777–785 (1979)]. The transfected cells were split 1:20 in normal medium at 24 hours post-transfection. After the cells were attached to the plate, the medium was changed to selective medium containing 1 mg/ml G418 (Sigma, St Louis, Mo.). The cells were refed with fresh selective medium every 3 days for about 2–3 weeks. Isolated clones were picked, expanded and maintained in the selective medium for 5–6 passages. The established 293-E4 cell lines were routinely maintained in the normal medium.

Example 3

Southern Transfers and Hybridization

Genomic DNA from 293-E4 cell lines were digested with desired restriction enzymes and purified with phenol/chloroform. 10 μg of digested DNA were run on 0.8%–1% agarose gel and transferred to a nylon membrane (Zetabind, America Bioanalytical, Natick, Mass.). DNA from the 293-E4 cell lines were digested with restriction enzymes and analyzed. DNA from wild type adenovirus 5, pIK6.1 MIP (α)-E4 plasmid and parental 293 cells were also digested with the same enzymes and used as controls. Restriction fragments of the E4 region, α-inhibin promoter sequence, and the E1 region were detected by hybridization to the appropriate $^{32}$P-labeled probes and subsequent autoradiography.

Example 4

Preparation of Viral Stocks

W162 cells were grown in DMEM, 4.5 g/L glucose and 10% CS. The W162 cell line is a Vero monkey kidney cell line transformed by adenovirus E4 DNA and supports the growth of E4 deleted adenovirus mutants [Weinberg, & Ketner, Proc. Natl. Acad. Sci. USA 80: 5383–5386 (1983)]. The H5dl1014 virus has been previously described in Bridge & Ketner, J. Virol. 63: 631–638, (1989). This adenovirus 5 virus strain has two deletions within the E4 region and can only grow in W162 cells (Bridge, & Ketner 1989). Propagation and titration of H5dl1014 virus were done on W162 cells. For evaluation of the production of H5dl1014 virus from 293-E4 cell lines of the present invention, the W162, 293 and 293-E4 cell lines were counted and plated in the 6-well plate at 1×10⁵/well and infected with H5dl1014 at a multiplicity of infection (m.o.i.) of 50 plaque-forming units (p.f.u.) per cell. The viral stocks were prepared by harvesting the cells at 48 hr post-infection. The cells were precipitated and resuspended in 200 μl of serum free medium. The cell suspensions underwent 3 cycles of freeze and were thawed to release the viral particles from the cells. The cell debris was discarded by centrifugation. The titers of the virus produced from the infected cells were determined by plaque formation on monolayers of W162 cells.

Example 5

Construction of Recombinant Viruses

The 293 cell line and 293-E4 cell line were plated in 10-cm plate at 2.5×10⁶/plate 48 hours before the experiment. One hour prior to the co-transfection, cells were fed with 10 ml fresh medium. Ad5/ΔE1(β-gal)ΔE3 virus was made by co-transfection of 10 μg of ADV-β-gal linearized by Bst BI with 4 μg of H5dl327 (Thimmappaya, et al, Cell 31: 543–551 1982) digested with Cla I. Ad5/ΔE1(β-gal)ΔE4 virus was generated by co-transfection of 10 μg of Bst BI linearized ADV-β-gal and 4 μg of Cla I digested H5dl1014 on 293-E4 cell lines by calcium phosphate precipitation technique. Twenty-four hours after co-transfection, the medium was removed and the monolayers of the culture were overlaid with 10 ml DMEM medium containing 20 mM MgCl₂, 5% of CS and 0.5% of noble agar (DIFCO Lab. Detroit, Mich.). The plaques were picked and resuspended in 100 μl of PBS. Diluted plaque samples were immediately subjected to 2 to 3 rounds of blue plaque purification. The blue plaque purification was carried out as a regular plaque assay except that the cultures were overlaid with a second layer of soft agar containing 1 mg/ml X-gal when plaques appeared. After incubation for 2 hours, plaques which contained the recombinant virus carrying the β-galactosidase gene were stained blue. The purity of the recombinant virus was determined by no contamination of white plaques. The purified plaques were expanded and the DNA of the lysate was analyzed (FIG. 6) as previously described [Graham & Prevec (1992)]. Adenoviral DNA was digested with Sma I and fractionated on 0.8% agarose gel. DNA samples of H5dl1014 and the Ad5/ΔE1(β-gal)ΔE3 viruses were extracted from CsCl gradient purified viral stocks. DNA of the Ad5/ΔE1(β-gal)ΔE4 was extracted from the virus infected cells.

Example 6

Histochemical Staining

Forty-eight hours following recombinant viral infection with Ad5/ΔE1(β-gal)ΔE3 virus (E1 and E3 deletion viruses) and Ad5/ΔE1(β-gal)ΔE4 virus (E1 and E4 deletion viruses) at 20 m.o.i. the monolayers of cells are washed once in PBS and fixed for 10 min. at room temperature with 0.5% glutaraldehyde (Sigma, St. Louis, Mo.) in PBS. The cells were washed three times with PBS containing 1 mM $MgCl_2$ and then stained with 5-bromo-4-chloro-3-indolyl-β, D-galactosidase (X-gal, Sigma) as previously described (Thimmappaya et al, 1982). The X-gal solution at 40 mg/ml in dimethylformamide was diluted to 1 mg/ml in KC solution (PBS containing 5 mM $K_3Fe(CN)_6$, 5 mM $K_4Fe(CN)_6 \cdot 3H_2O$). After staining, for 2–4 hours the cells were washed with $H_2O$ and inspected under a light microscope.

Example 7

β-galactosidase Activity Assay

Cells were infected with either Ad5/ΔE1(β-gal)ΔE3 virus and Ad5/ΔE1(β-gal)ΔE4 virus at 20 m.o.i. assayed for enzyme activity as described in MacGregor, et al, *Somatic Cell Mol. Genetic.* 13: 253–264, (1987) with the following modifications. Cells in 6-well plate were washed with PBS twice and lysed in the well by addition of 200 μl of 2× Z buffer (1× Z buffer: 60 mM $Na_2PO_4 \cdot 7H_2O$, 40 mM $NaH_2PO_4 \cdot H_2O$, 10 mM KCl, 1 mM $MgSO_4 \cdot 7H_2O$) and 200 μl of 0.2% Triton X-100. After incubation at room temperature for 5–10 min, 100 μl of each sample was transferred to the 96-well microtiter plate. After addition of 50 μl of 2-nitrophenyl-β-D-galactopyranoside (2mg/ml), the reaction was allowed to proceed for 5 min at room temperature and stopped by adding 50 μl of stop solution (1M $Na_2CO_3$). Fluorescence was measured at 420 nm on a microtiter plate reader (Molecular Devices Co. Menlo Park, Calif.).

Example 8

Construction of 293-E4 Cell Lines

Figure 1:
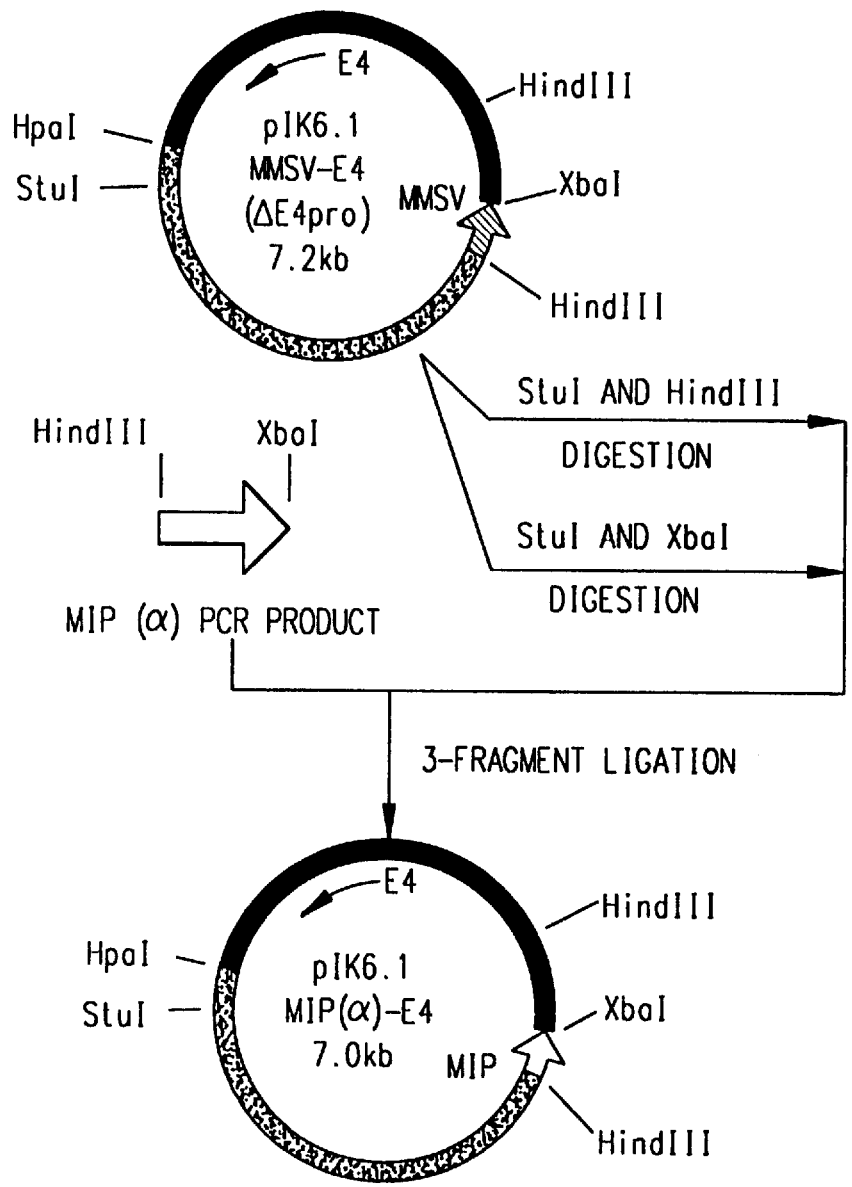
FIG. 1 depicts the construction of the pIK.6.1 MIP($\alpha$)-E4 plasmid, as described in Example 1, infra.

The purpose of introducing the Ad5 E4 gene region into 293 cells is that the derived cell line is able to package the recombinant adenoviruses containing two lethal deletions (E1 and E4). The plasmid, PIk.MIP(α)-E4 carries the full length region of the Ad5 E4 region from 15 bp upstream of transcription start site to 810 bp downstream of the polyadenylation site (FIG. 1). The E4 gene region (m.u. 88.9–98.8) was directly linked to 238 bps of the mouse α-inhibin promoter containing the first 159 bps of the promoter region and 5' untranslated region. This promoter sequence is required for basal expression (Su & Hseuh (1992)). Within this promoter region, there is a cyclic adenosine 3', 5'-monophosphate (cAMP) response element (CRE) which allows an increased level of gene expression induced by either cAMP or adenylic cyclase activator [Paei, et al, *Mol. Endocrinol.* 5: 521–534 (1991)]. The pIK.MIP (α)-E4 was introduced into 293 cells together with the PGEM-pgkNeo.pghpolyA which bears a neomycin resistant gene by calcium phosphate precipitation at a molar ratio equivalent to 10:1. A total of 66 G418 resistant clones were picked for further analysis.

Example 9

Identification of E4 Transfectants

Figure 3A:
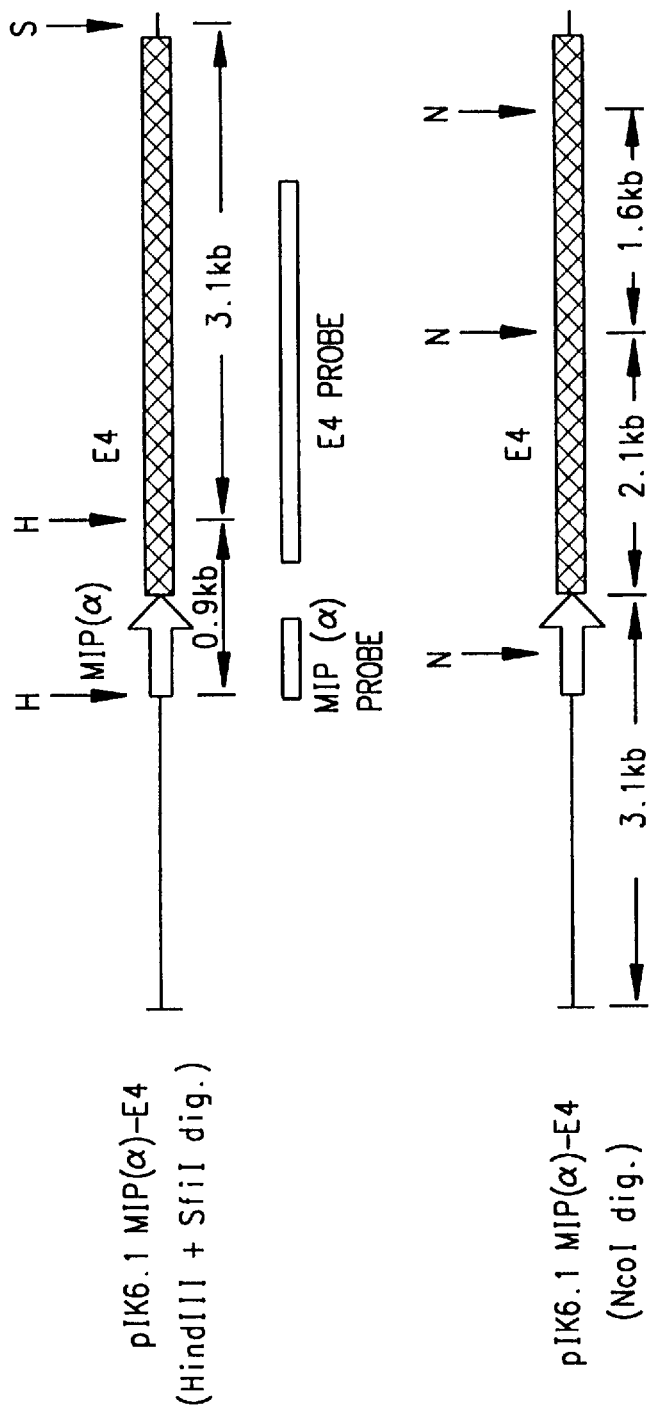
FIGS. 3(A)–(E) are illustrations and the Southern analysis of 293-E4 cell lines as described in Example 3, infra. (A) The restriction patterns of the introduced MIP($\alpha$)-E4 and the probes used in Southern blots are depicted in this illustration. The solid arrow represents the mouse $\alpha$-inhibin promoter region. The open box represents the full length of the E4 region. The mouse inhibin probe is the 283 bp PCR product described in Example 1. The E4 probe is the Sma I H fragment (m.u. 92 to 98.4). Restriction enzyme sites are abbreviated as follows: H, Hind III; S, Sfi I; N, Nco I. (B) DNA was digested with Hind III and Sfi I and hybridized to the E4 probe. (C) DNA was digested with Nco I and hybridized to the E4 probe. (D) The E4 probe was stripped from Hind III and Sfi I digestion blot and the DNA was reprobed with the inhibin promoter probe. (E) The inhibin probe was washed off from the Hind III and Sfi I digestion blot and DNA was reprobed with the E1 probe which is a Hind III E fragment from m.u. 7.7 to m.u. 17.1.
Figure 3B:
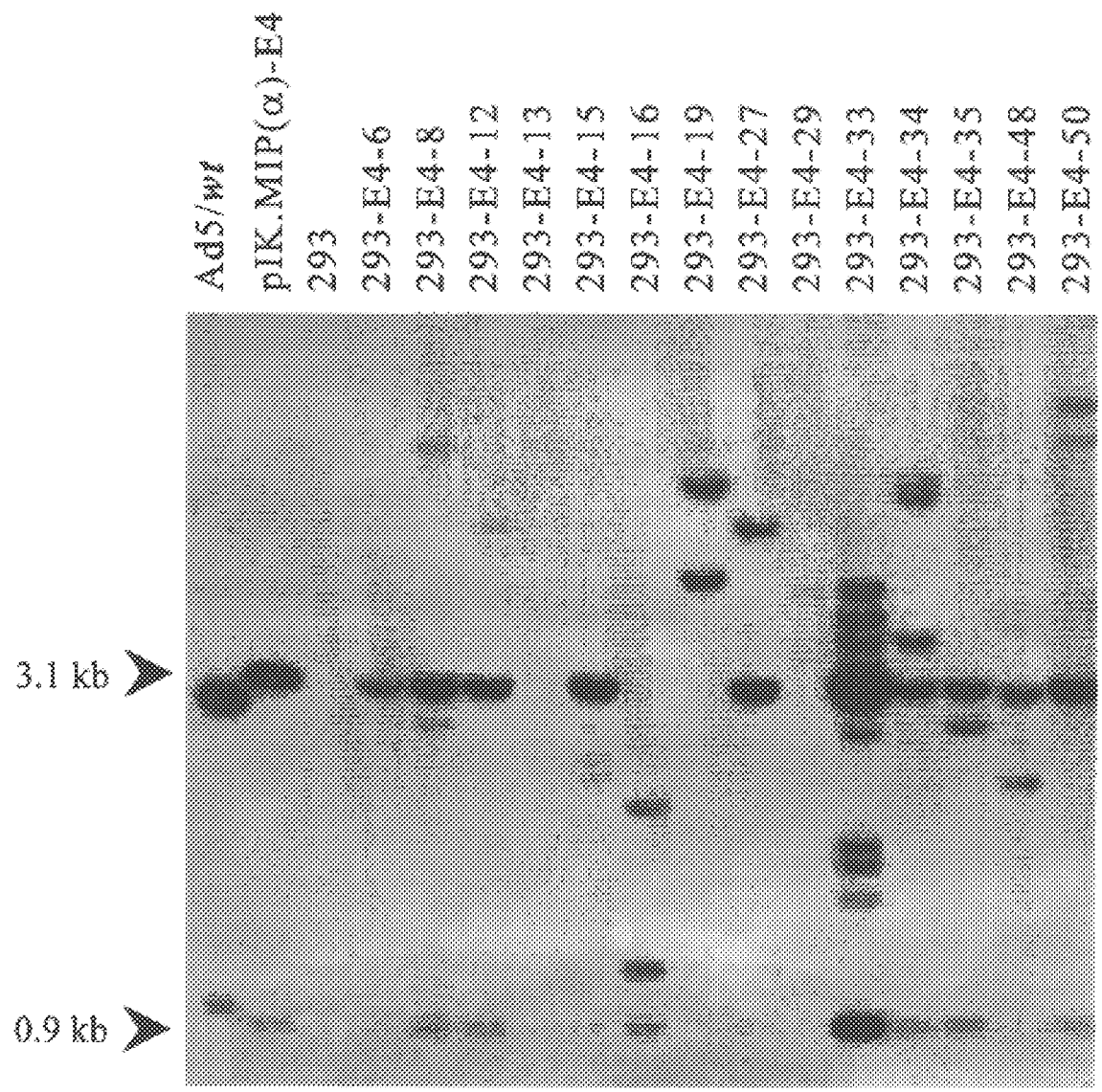
Figure 3C:
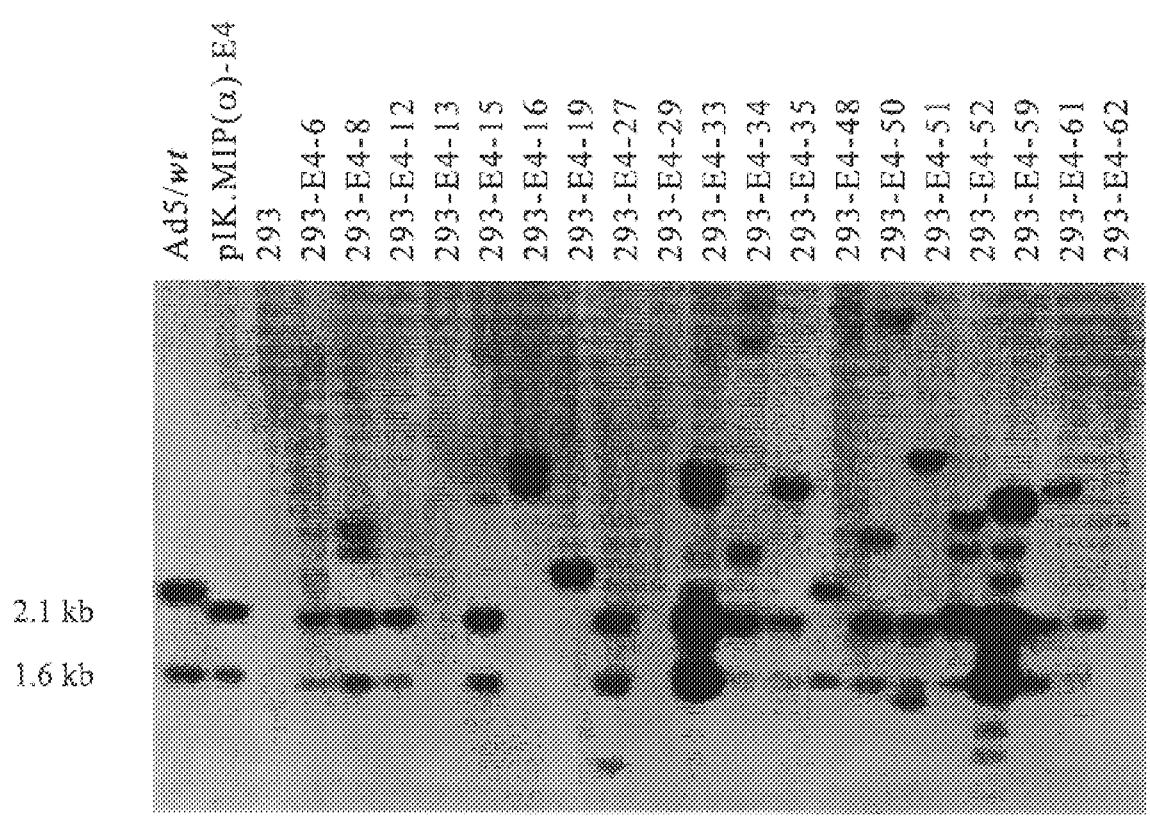
Figure 3D:
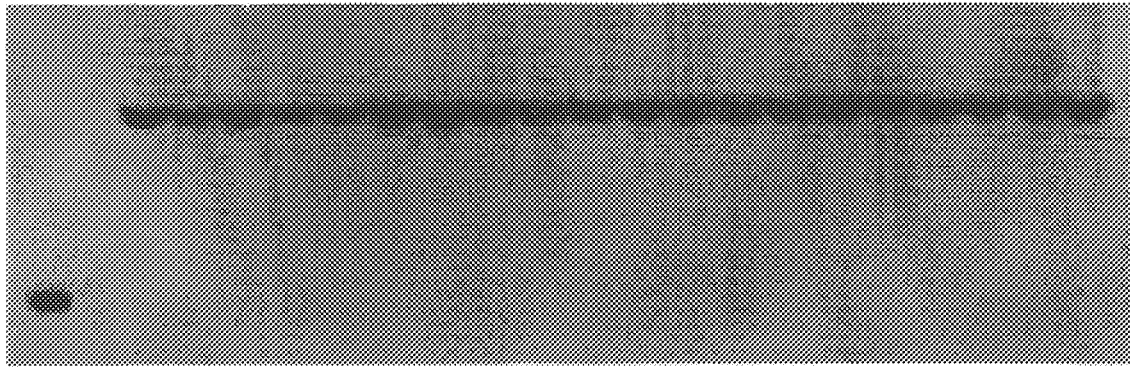
Figure 3E:
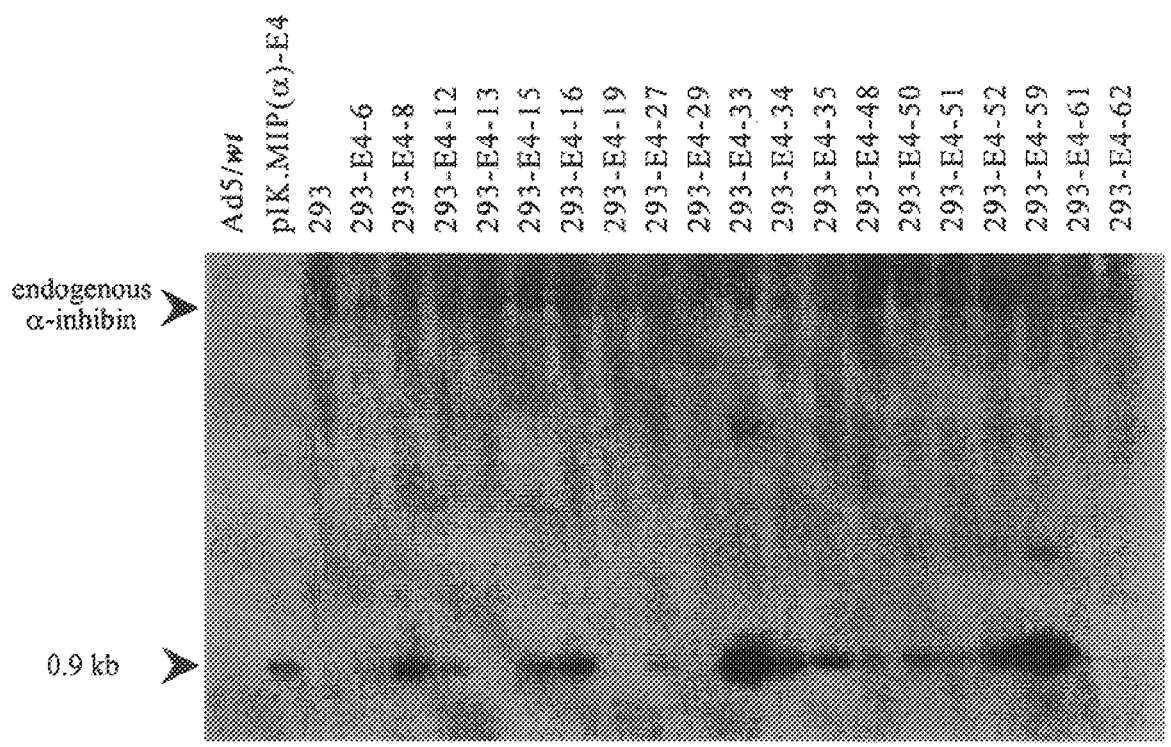
Figure 4A:
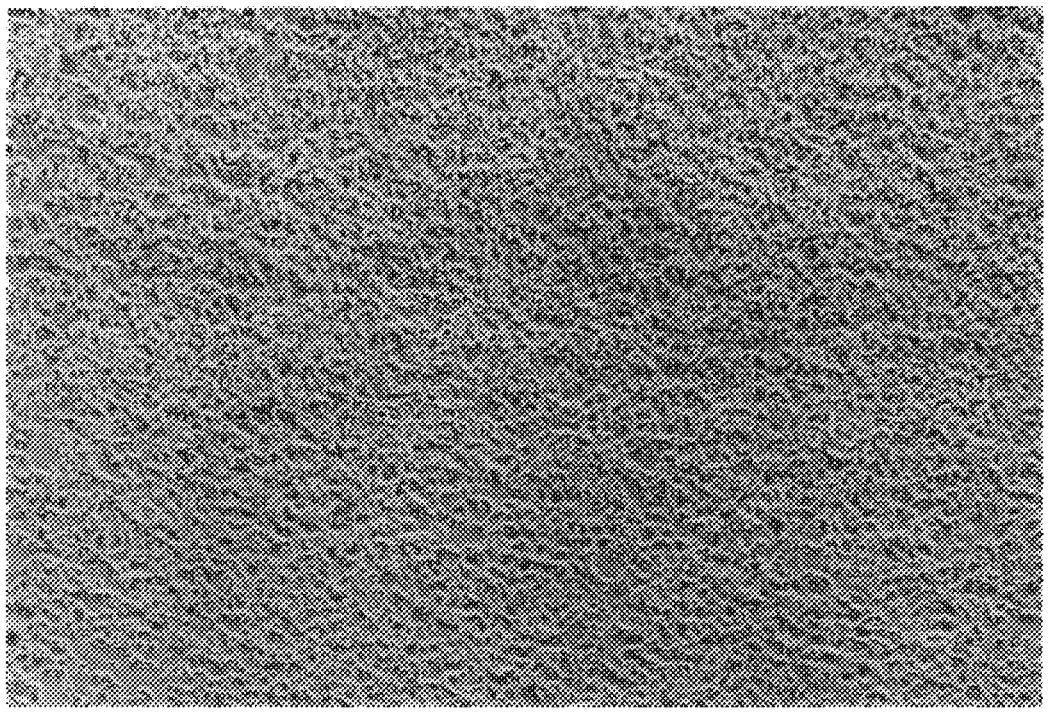
FIGS. 4A–J are photographs showing the cytopathic effect of H5dl1014 on W162, 293 and 293-E4 cell lines in the presence or absence of cAMP, as described in Example 10, infra. Parental 293 cells are represented in panels A–D; 293-E4 cells are represented in panels E–G and W162 cells are represented in panels H–J. The cells without infection are shown in panels A, E and H. The cells infected with H5dl1014 without an addition of cAMP are shown in panels C, F and I and the cells infected with H5dl1014 with an addition of 1 mM cAMP are shown in panels D, G and J.
Figure 4B:
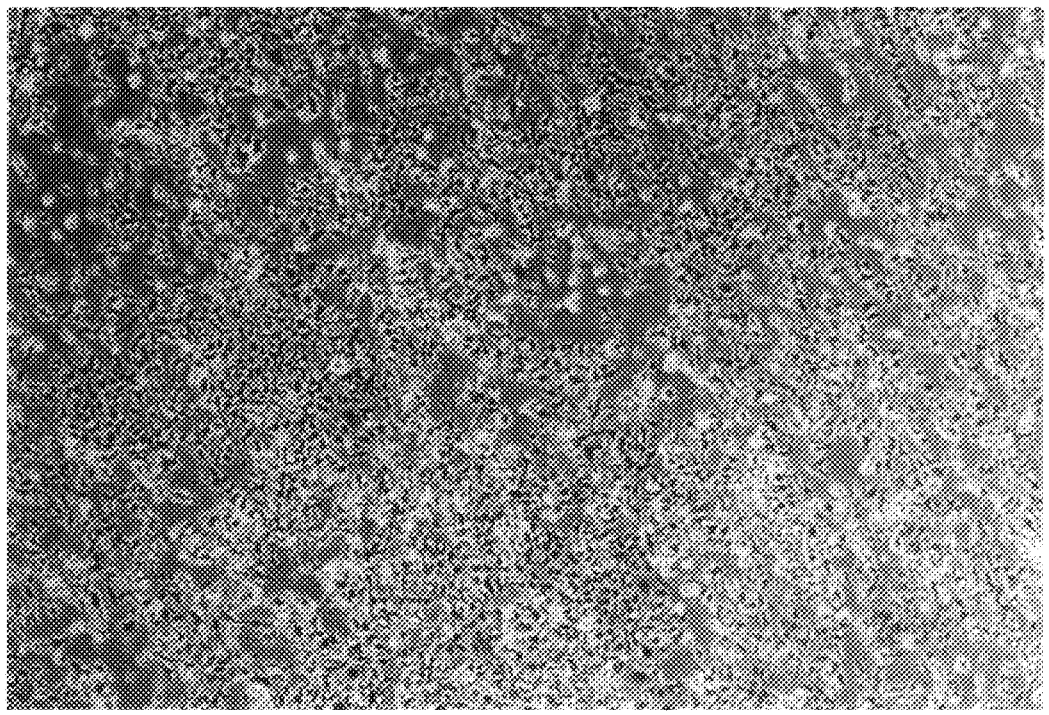
Figure 4C:
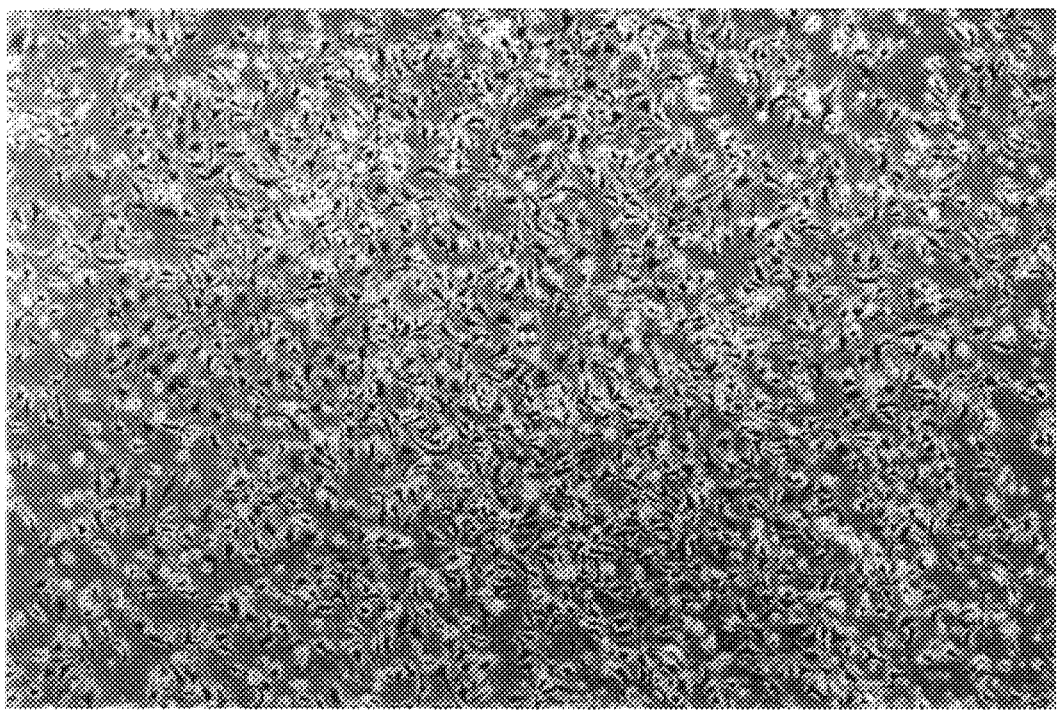
Figure 4D:
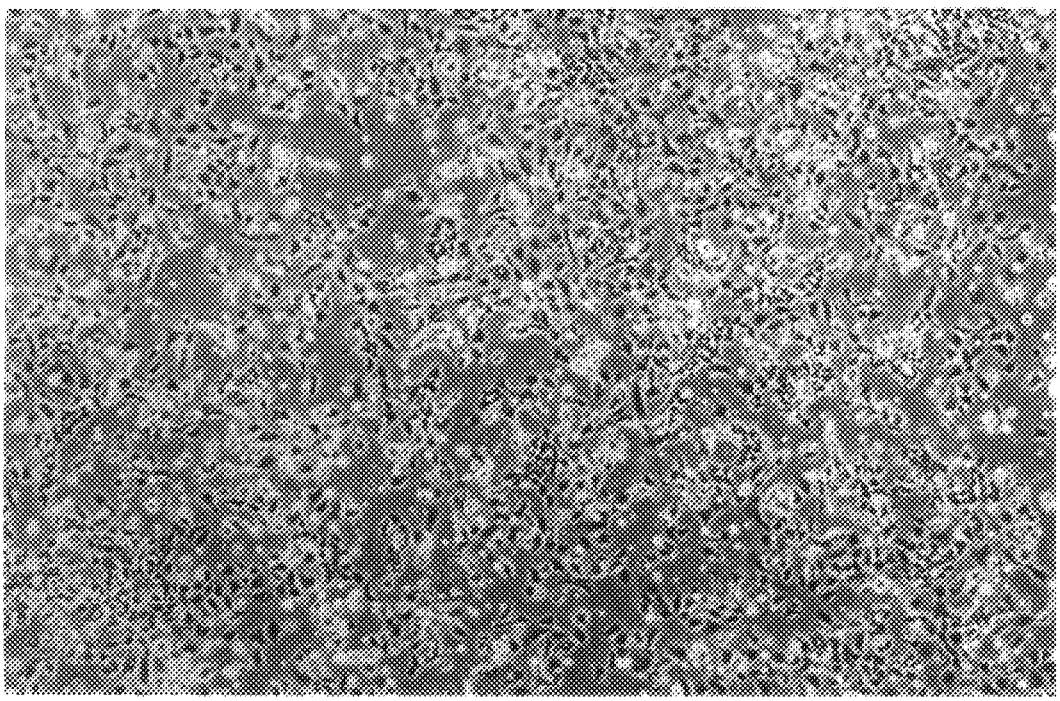
Figure 4E:
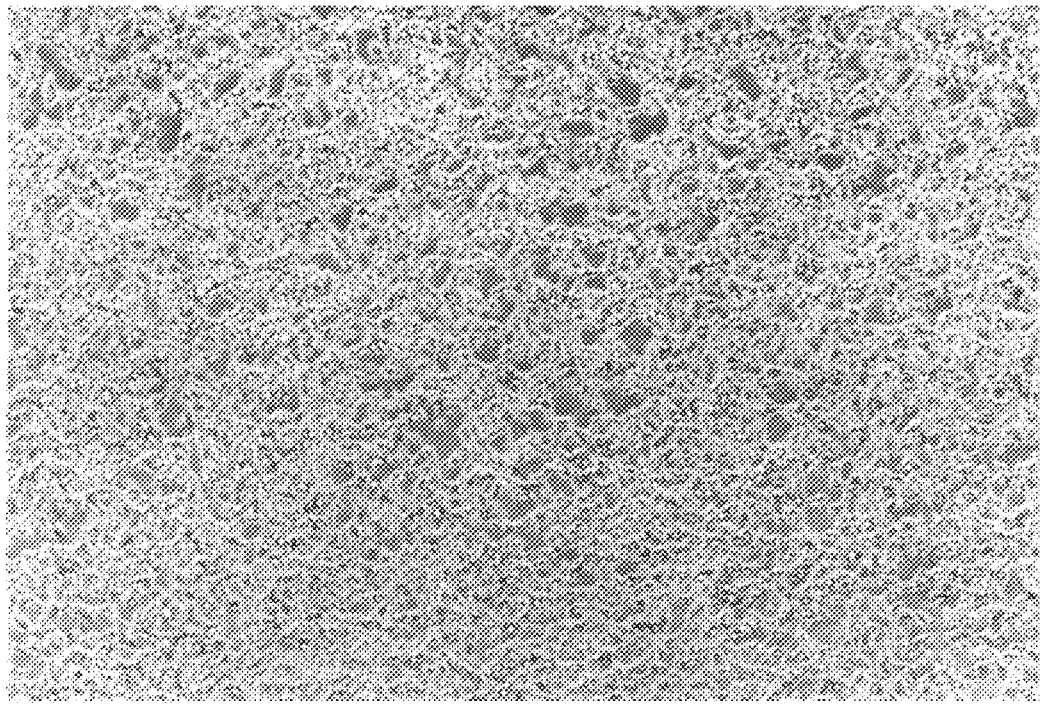
Figure 4F:
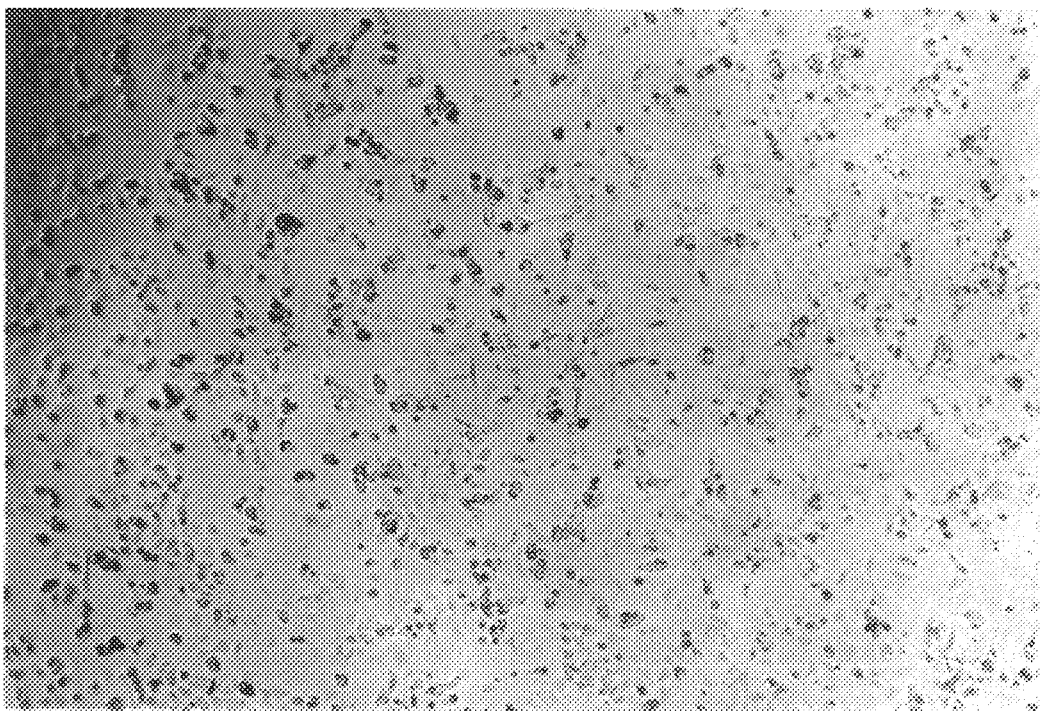
Figure 4G:
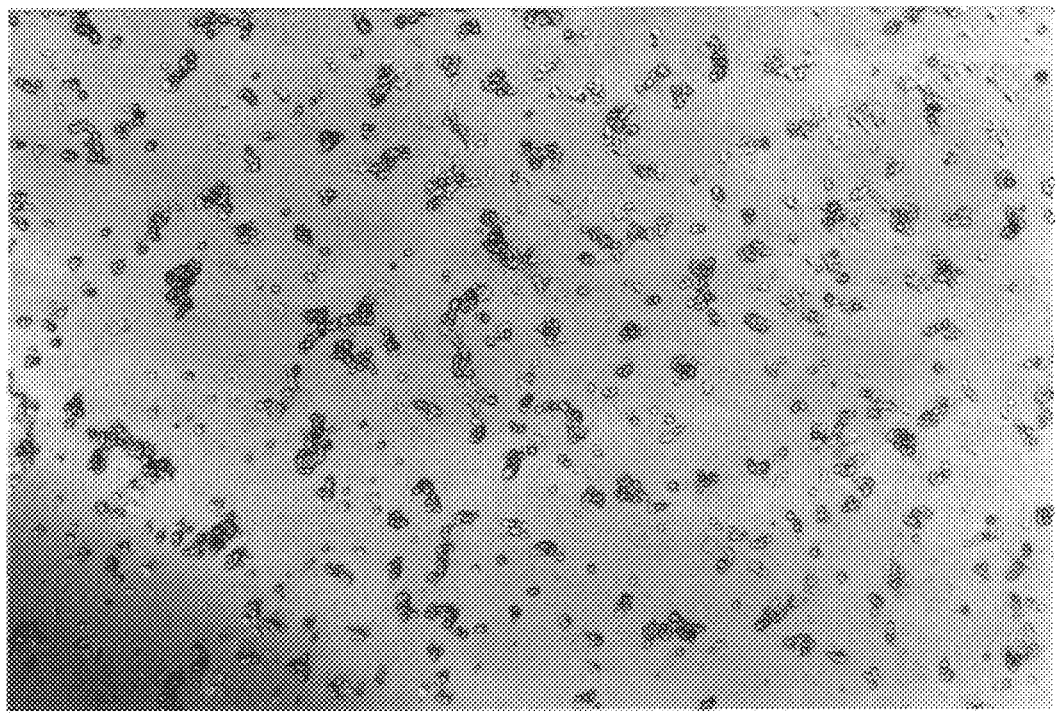
Figure 4H:
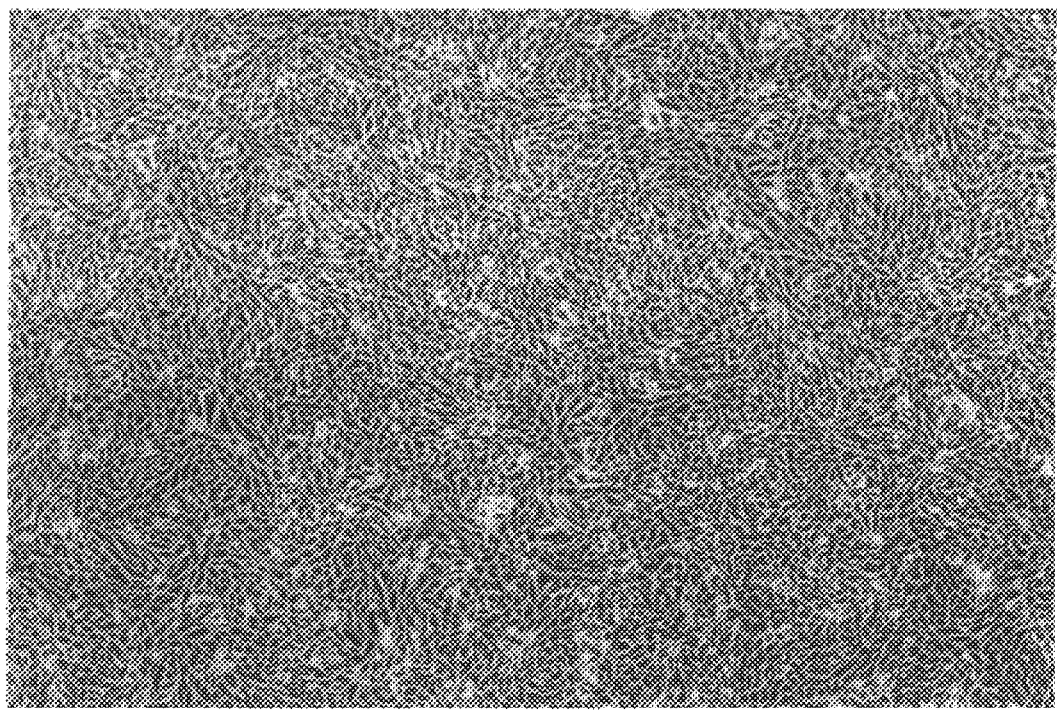
Figure 4I:
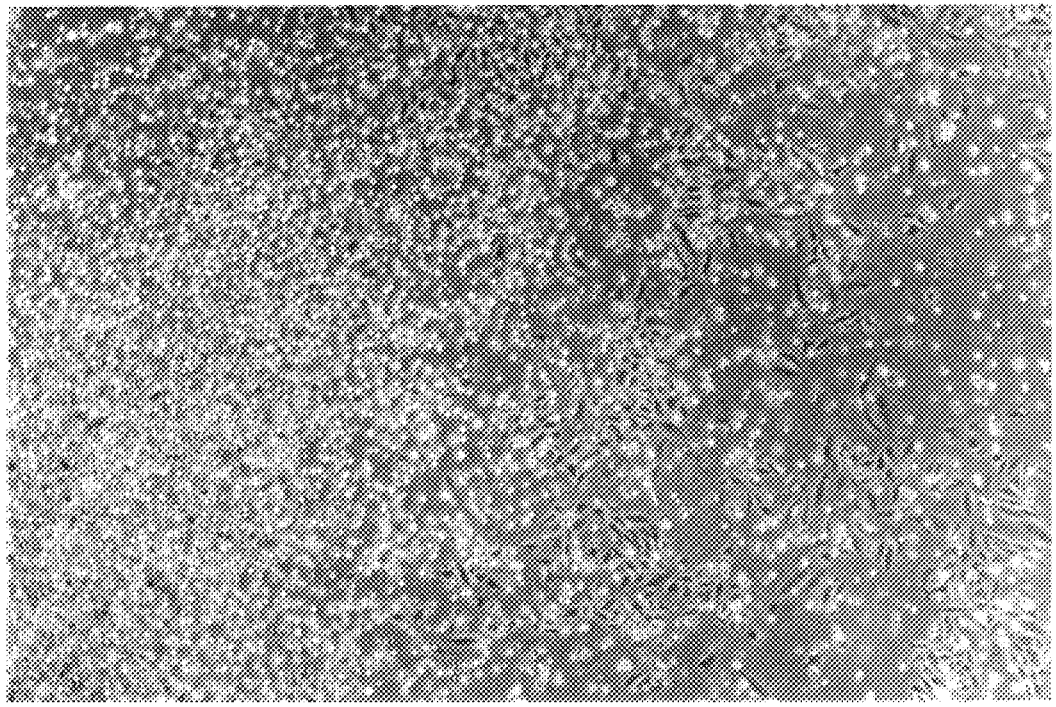
Figure 4J:
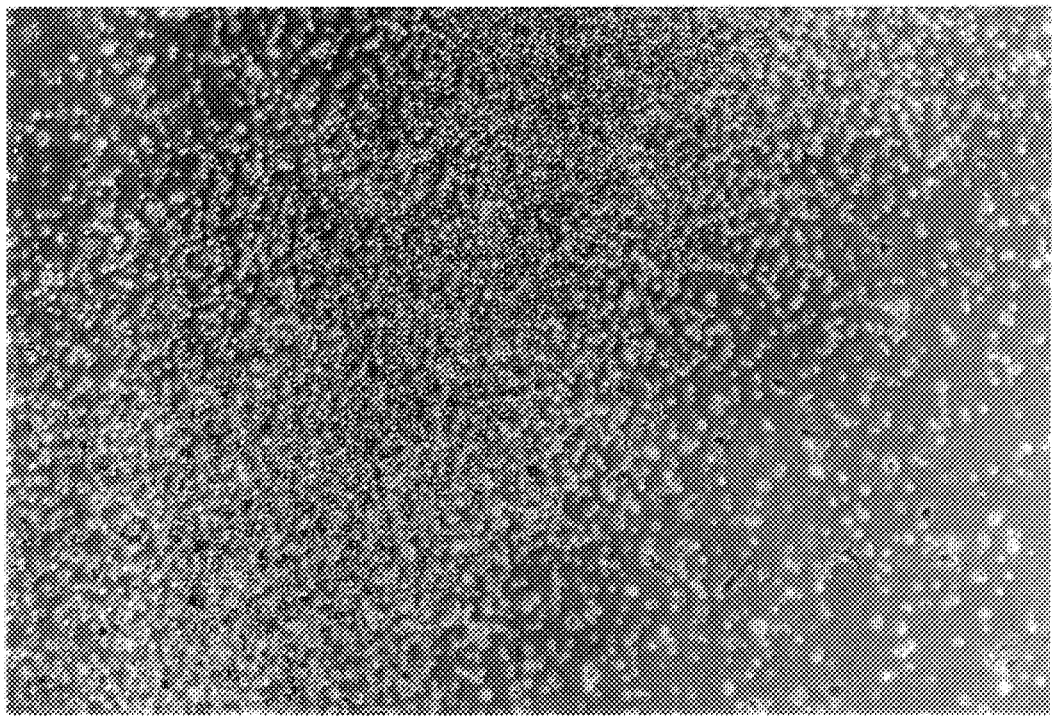

To examine the integration of the introduced adenovirus E4 region, genomic DNA from each clone was digested with either Hind III and Sfi I, or Nco I restriction enzymes and analyzed by Southern transfer. FIG. 3A shows a restriction map of the introduced α-inhibin-E4 region and corresponding regions of the E4 probe (Sma I H fragment of Ad5) and the inhibin promoter probe. 17 clones out of a total of 66 presented the correct DNA patterns as predicted for a full length E4 region DNA integration in the screen blots of both digestions. Other clones showed either no integration or integration with variable sizes of E4 region. FIGS. 3B–3E represent the Southern blots of genomic DNA extracted from the 17 clones with full length integration and two clones which contains variable sizes of E4 region integration on the initial screening blots. The DNA was extracted after maintaining these 19 cell lines in the non-selective medium for more than 30 passages. As shown in FIGS. 3B and 3C, 15 cell lines represent the characteristic 0.9 kb and 3.2 kb fragments in HindIII/Sfi I digestion and 1.6 kb and 2.1 kb fragments in Nco I digestion. There were no detectable E4 region sequences in two cell lines (lines 13 and 29) which had the same integration patterns as the other 15 lines in the screening blots, indicating an unstable integration event in these two lines. Lines 16 and 19 are examples of cell lines which retained the E4 gene region with variable restriction patterns. The 0.9 kb band of all 15 lines hybridized to the mouse inhibin promoter sequence in the Hind III/Sfi digestion (FIG. 3D). The 3.1 kb fragment along with the 2.1 kb fragment was hybridized to the inhibin promoter probe in the Nco I digestion blot. These results indicate that a full length gene region of E4 was stably integrated into these 15 cell lines. To rule out the possibility that these cell lines can survive and maintain a full length of the E4 region due to a loss of the E1 gene region, the blots were reprobed with the Ad5 Hind III E fragment (m.u. 7.7–17.1). All 19 lines have a same sized fragment detected by the E1 probe as that in the parental 293 cell line (FIG. 3E). Therefore, the E1 gene was not altered in the 293-E4 cell lines.

Example 10

Screen of Biological Activity of 293-E4 Cell Lines

To determine whether these cell lines were capable of supporting the E4 deletion virus growth, each of the cell lines was infected with an adenovirus E4 deletion mutant virus H5dl1014 [Bridge & Ketner, (1989)]. The E4 defective strain H5dl1014 contains two deletions from m.u. 92 to 93.8 and m.u. 96.4 to 98.4. The deletions destroy all the open reading frames of the E4, region except ORF 4. This virus produces substantially less viral DNA and late viral proteins in Hela cells similar to that seen in cells infected with H2dl808 and H5dl366 [Halbert, et al, *J. Virol.* 56: 250–256 (1985)]. The only permissive cell line for the growth of H5dl1014 is W162 [Weinberg & Ketner, (1983)]. When the parental 293 cells, W162 cells and all 15 lines were infected with H5dl1014 at m.o.i. 25 with or without addition of the 1 mM cAMP, 6 cell lines showed comparable cytopathic effect (CPE) as observed on W162 cells at 3–4 days of post-infection (FIG. 4). The CPE appeared much faster in the presence of cAMP both in W162 cells and in some of the 293-E4 cell lines. The parental 293 cells showed CPE at much milder level (FIG. 4). This result shows that 293-E4 cell lines (containing both E1 and E4 gene regions) support the growth of E4 deleted viruses (eg., H5dl1014 virus) as efficiently as cell lines containing the E4 gene region only (eg., W162 cell line).

Example 11

Induction of H5dl1014 Production On 293-E4 Cell Lines

To quantitatively examine the ability of 293-E4 cell lines to produce H5dl1014 mutant virus and to determine whether there is a specific induction of E4 gene expression in the 293-E4 cell lines, the titer of the H5dl1014 produced from the 293-E4 cell lines was measured in the presence or absence of cAMP. Viral stocks were prepared from each cell line by infecting the same number of cells with H51014 at m.o.i. 50. At 48 hr post-infection, the supernatant of each cell line was removed and the cells were resuspended in ⅒ of the original volume of serum free medium. Titration of the viral stocks were performed on W162 cells by plaque assay. As presented in Table 1, the phenomenon of virus production from these 15 lines can be generally classified into three groups. Group 1 which includes lines 8, 50 and 51 showed increased viral titers by 4 to 6 orders of magnitude compared to the titer produced from 293 cells. Line 8 and 51 had a 10 fold increase of the viral titers in the presence of cAMP. Group 2, which includes lines 12, 27 and 61, produced similar titers of virus as that produced from W162 cells. The titers increased 1,000–10,000 fold with the exception of line 12 in which the level of virus production increased by 7 orders of magnitude in the presence of cAMP. These results indicate an induced E4 gene expression in these three cell lines. Group 3 includes the remaining cell lines which produced the virus titers essentially at levels similar to that produced from parental 293 cells in the presence or absence of cAMP. The induced E4 gene expression is also indicated in several cell lines in this group.

The 10 fold induction was also observed in the W162 cells and parental 293 cells when the cells were treated with cAMP. It is possible that this 10 fold increase in the virus yield is due to the enhancement effect of cAMP on other adenovirus early gene expression [Leza & Hearing, *J. Virol.* 63: 3057–3064 (1989)] which also contains CRE elements causing an increase in viral DNA synthesis.

TABLE IV

Titers of H5dl1014 produced from cell lines W162, 293, and 293-E4

| GROUP | CELL LINE | TITER [pfu/ml]† No cAMP | 1mM cAMP |
|---|---|---|---|
| control | W162 | $2.2 \times 10^{13}$ | $1.2 \times 10^{14}$ |
|  | 293 | $1.6 \times 10^{4}$ | $2.7 \times 10^{5}$ |
| 1 | 293-E4-8 | $8.9 \times 10^{12}$ | $3.3 \times 10^{13}$ |
|  | 293-E4-50 | $6.7 \times 10^{10}$ | $4.5 \times 10^{10}$ |
|  | 293-E4-51 | $8.9 \times 10^{8}$ | $2.2 \times 10^{9}$ |

TABLE IV-continued

Titers of H5dl1014 produced from cell lines W162, 293, and 293-E4

| GROUP | CELL LINE | TITER [pfu/ml]† No cAMP | 1mM cAMP |
|---|---|---|---|
| 2 | 293-E4-12 | $4.5 \times 10^{5}$ | $8.9 \times 10^{12}$ |
|  | 293-E4-27 | $6.7 \times 10^{9}$ | $2.2 \times 10^{13}$ |
|  | 293-E4-61 | $1.3 \times 10^{10}$ | $8.0 \times 10^{13}$ |
| 3 | 293-E4-6 | $1.1 \times 10^{4}$ | $8.9 \times 10^{4}$ |
|  | 293-E4-15 | $1.3 \times 10^{5}$ | $6.7 \times 10^{6}$ |
|  | 293-E4-33 | $6.7 \times 10^{4}$ | $1.6 \times 10^{6}$ |
|  | 293-E4-34 | $6.7 \times 10^{6}$ | $1.3 \times 10^{7}$ |
|  | 293-E4-35 | $1.3 \times 10^{5}$ | $1.1 \times 10^{6}$ |
|  | 293-E4-48 | $6.7 \times 10^{4}$ | $6.7 \times 10^{6}$ |
|  | 293-E4-52 | $1.8 \times 10^{4}$ | $1.3 \times 10^{7}$ |
|  | 293-E4-59 | $3.3 \times 10^{3}$ | $6.7 \times 10^{6}$ |
|  | 293-E4-62 | $1.6 \times 10^{5}$ | $6.7 \times 10^{6}$ |

†The titer was determined by plaque assay on W162 monolayer culture. Values in the table are the averages of titers measured on duplicate samples.

Example 12

Generation of Ad5/ΔE1 (β-gal)ΔE4 Virus

To rescue recombinant virus which harbors lethal deletions in both the E1 region and the E4 region the two most efficient cell lines, line 8 and line 61, were utilized. The ADV-β-gal plasmid was linearized by BstBl and co-transfected with Cla I digested H5dl1014 into the monolayers of 293-E4 cell lines (FIG. 5). The recombinant virus was generated by in vivo recombination between the overlapping adenoviral sequence of ADV-β-gal and the H5dl1014 large Cla I fragment (m.u. 2.55–100). Plaques appearing at 7–10 days post-transfection were isolated and purified by blue plaque assay. The final purified blue plaque and the viral DNA were analyzed (FIG. 6). For the following comparative studies of the double deletion recombinant virus, the Ad5/ΔE1(β-gal)ΔE3 virus was generated. This virus was generated by co-transfection of Bst BI linearized ADV-β-gal plasmid with Cla I digested H5dl327 [Thimmappaya, et al, (1982)] into 293 cells (FIG. 5).

Example 13

In Vitro Evaluation of the Ad5/ΔE1(β-gal)ΔE4 Virus

To evaluate the infectivity of this second generation of recombinant virus, infectivity was compared with the β-gal gene expression of the double lethal deletion virus and single lethal deletion virus in Hela, 293, W162 and line 61 cells. The cells were infected with these two strains of recombinant viruses at 20 m.o.i. for 48 hrs. Expression was observed in both infections as detected both by histochemical staining and the β-galactosidase activity assay described supra. The abolished cytopathic effect of the Ad5/ΔE1(β-gal)ΔE4 virus was also tested by the plaque assay. The 293-E4 was the only permissive cell line for all three strains of virus (Ad5/ΔE1(β-gal)ΔE4, Ad5/ΔE1(β-gal)ΔE3 and H5dl1014). The 293 cells were permissive for the Ad5/ΔE1 (β-gal)ΔE3 virus, semi-permissive (low level of virus production) for the H5dl1014 virus but non-permissive to Ad5/ΔE1(β-gal)ΔE4 virus. The W162 cell line was permissive for H5dl1014 virus, but non-permissive for Ad5/ΔE1 (β-gal)ΔE3 virus and Ad5/ΔE1(β-gal)ΔE4 virus. Hela cells are non-permissive for all three strains of viruses. These results demonstrate that the double deletion virus does not cause any cytopathic effect to the human cell lines tested. Absence of cytopathic effects following infection of the double deletion viruses at m.o.i. 20 suggests that in vivo these viruses will not express late gene products. This should eliminate the immune response against cells infected with recombinant virus, thereby prolonging transgene expression.

All publications cited in this specification are herein incorporated by reference in their entirety as if each individual publication was specifically and individually indicated to be incorporated by reference.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the invention is as set forth in the appended claims rather than being limited to the examples contained in the foregoing description.

We claim:

1. A packaging cell line that supports the replication of a mutant, replication-defective adeno-associated virus stock, wherein said packaging cell line is free of helper adenoviruses and comprises an adenoviral E2A and E4 early gene region each operably linked to a non-adenoviral promoter, an E1 early gene region and DNA encoding VA-RNA.

2. A packaging cell line that supports the replication of a recombinant, replication-defective adeno-associated virus stock, wherein said packaging cell line is free of helper adenovirus and comprises an adenoviral E2A and E4 early region each operably linked to a non-adenoviral promoter, an E1 early gene region and a VA-RNA sequence.

3. A packaging cell line that supports the replication of a mutant adeno-associated virus carrying a deletion of the rep gene region, to produce a replication-defective adeno-associated virus stock, wherein said packaging cell line is free of helper adenovirus and comprises an adenoviral E2A and E4 early gene region each operably linked to a non-adenoviral promoter, an adenoviral E1 early gene region, a VA-RNA sequence, adeno-associated virus rep gene region, and optionally an adenoviral E3 early gene region.

4. A packaging cell line that supports the replication of a recombinant adeno-associated virus carrying a deletion of the rep gene region to produce a replication-defective adeno-associated virus stock, wherein said packaging cell line comprises an adenoviral E2A and E4 early gene region each operably linked to a non-adenoviral promoter, an adenoviral E1 early gene region, a DNA sequence encoding VA-RNA, an adeno-associated virus rep gene region, and optionally an adenoviral E3 early gene region.

5. A packaging cell line that supports the replication of a mutant adeno-associated virus carrying a deletion of the rep gene region and the cap gene region to produce a replication-defective adeno-associated virus stock, wherein said packaging cell line comprises an adenoviral E2A and E4 early gene region each operably linked to a non-adenoviral promoter, an adenoviral E1 early gene region, a VA-RNA sequence, an adeno-associated virus rep gene region, an adeno-associated virus cap gene region and optionally an adenoviral E3 early gene region.

6. A packaging cell line that supports the replication of a recombinant adeno-associated virus carrying a deletion of the rep gene region and the cap gene region to produce a replication-defective adeno-associated virus stock, wherein said packaging cell line comprises an adenoviral E2A and E4 early gene region each operably linked to a non-adenoviral promoter, an adenoviral E1 early gene region, a DNA sequence encoding VA-RNA, an adeno-associated virus rep gene, an adeno-associated virus cap gene region, and optionally an adenoviral E3 early gene region.

7. A packaging cell line that supports the replication of a mutant, replication-defective adeno-associated virus stock, wherein said packaging cell line is free of helper adenovirus, and contains portions of the adenoviral genome selected from the group consisting of E1, E2A and E4 early gene regions, and DNA encoding VA-RNA.

8. A packaging cell line that supports the replication of a mutant, replication-defective adeno-associated virus stock in the absence of wild-type adenovirus, wherein said packaging cell line is free of helper adenovirus and comprises adenoviral E1, E2A and E4 early gene regions, and DNA encoding VA-RNA.

9. A packaging cell line that supports the replication of a mutant, replication-defective adeno-associated virus stock, wherein said packaging cell line consists of adenoviral E1, E2A and E4 early gene regions and DNA encoding VA-RNA.

10. The packaging cell line of claim 1, 2, 3, 4, 5 or 6 wherein the non-adenoviral promoter is an inducible promoter.

11. A DNA plasmid comprising an adeno-associated viral gene operably linked to an inducible promoter containing a cAMP response element.

12. The DNA plasmid of claim 11 in which the promoter is regulated by a CRE binding protein.

13. The DNA plasmid of claim 11 in which the inducible promoter is a mammalian alpha inhibin promoter.

14. The DNA plasmid of claim 12 in which the inducible promoter is a murine alpha inhibin promoter.

15. The DNA plasmid of claim 11, 12, 13 or 14, in which the adeno-associated viral gene is the rep gene or the cap gene.

* * * * *